US012599770B1

(12) United States Patent
Peterson et al.

(10) Patent No.: US 12,599,770 B1
(45) Date of Patent: Apr. 14, 2026

(54) ENERGY EFFICIENT ELECTRICAL PULSE GENERATING DEVICE

(71) Applicant: Axonics, Inc., Irvine, CA (US)

(72) Inventors: Pete Peterson, Irvine, CA (US); Steve Wood, Irvine, CA (US)

(73) Assignee: Axonics, Inc., Irvine, CA (US)

( * ) Notice: Subject to any disclaimer, the term of this patent is extended or adjusted under 35 U.S.C. 154(b) by 707 days.

(21) Appl. No.: 17/896,021

(22) Filed: Aug. 25, 2022

(51) Int. Cl.
A61N 1/36 (2006.01)
A61N 1/04 (2006.01)

(52) U.S. Cl.
CPC ..... *A61N 1/36125* (2013.01); *A61N 1/36157* (2013.01); *A61N 1/04* (2013.01)

(58) Field of Classification Search
CPC ... A61N 1/36125; A61N 1/36157; A61N 1/04
See application file for complete search history.

(56) References Cited

U.S. PATENT DOCUMENTS

| | | | |
|---|---|---|---|
| 7,444,181 B2 | 10/2008 | Shi et al. | |
| 7,483,747 B2 | 1/2009 | Gliner et al. | |
| 8,131,358 B2 | 3/2012 | Moffitt et al. | |
| 8,311,639 B2 | 11/2012 | Parker et al. | |
| 8,457,759 B2 | 6/2013 | Parker et al. | |
| 8,515,545 B2 | 8/2013 | Trier | |
| 8,655,453 B2 | 2/2014 | Werder et al. | |
| 8,918,174 B2 | 12/2014 | Woods et al. | |
| 8,918,177 B2 | 12/2014 | Gauthier | |
| 9,031,664 B2 | 5/2015 | Trier | |

| | | |
|---|---|---|
| 9,320,899 B2 | 4/2016 | Parramon et al. |
| 9,731,116 B2 | 8/2017 | Chen |
| 9,744,347 B2 | 8/2017 | Chen et al. |
| 9,764,147 B2 | 9/2017 | Torgerson |
| 9,776,006 B2 | 10/2017 | Parker et al. |
| 9,925,381 B2 | 3/2018 | Nassif |
| 10,173,062 B2 | 1/2019 | Parker |

(Continued)

FOREIGN PATENT DOCUMENTS

WO        2011088130 A2        7/2011

OTHER PUBLICATIONS

Shiau-Pin Lin et al; "Design of Stage-Selective Negative Voltage Generator to Improve On-Chip Power Conversion Efficiency for Neuron Stimulation"; IEEE Transactions on Circuits and Systems-I: Regular Papers, vol. 67, No. 11; Nov. 2020; pp. 4122-4131.

*Primary Examiner* — Carl H Layno
*Assistant Examiner* — Aya Ziad Bakkar
(74) *Attorney, Agent, or Firm* — Seager Tufte & Wickhem, LLP

(57) ABSTRACT

According to another disclosed embodiment, an energy efficient implantable neurostimulator for delivering one or more electrical pulses to a target region within a patient's body is provided. The neurostimulator includes a converter for generating the stimulation current, wherein the converter includes a voltage increasing circuit and a voltage reducing circuit. The stimulator may also include a current source that includes a pair of cascode arranged transistors that are controlled to maintain an amplitude of the stimulation current substantially constant. The neurostimulator may also include a bias voltage power supply that powers a selecting circuit for selecting one of the voltage increasing or voltage decreasing circuits.

15 Claims, 14 Drawing Sheets

(56)                    References Cited

U.S. PATENT DOCUMENTS

| | | | |
|---|---|---|---|
| 10,195,425 B2 | 2/2019 | Ostroff et al. | |
| 10,384,054 B2 | 8/2019 | Chen | |
| 10,456,574 B2 | 10/2019 | Chen et al. | |
| 10,850,104 B2 | 12/2020 | Nassif | |
| 2004/0186526 A1* | 9/2004 | Freeberg | A61N 1/36521 |
| | | | 607/17 |
| 2007/0066995 A1 | 3/2007 | Strother et al. | |
| 2007/0191907 A1 | 8/2007 | Stein et al. | |
| 2008/0058901 A1 | 3/2008 | Ternes et al. | |
| 2010/0106219 A1* | 4/2010 | Torgerson | A61N 1/36185 |
| | | | 607/59 |
| 2010/0268309 A1 | 10/2010 | Parramon et al. | |
| 2011/0077698 A1 | 3/2011 | Tsampazis et al. | |
| 2014/0214128 A1 | 7/2014 | Peterson et al. | |
| 2017/0232260 A1 | 8/2017 | Chen | |
| 2020/0155841 A1 | 5/2020 | Bhagat et al. | |
| 2020/0368534 A1 | 11/2020 | Nassif | |
| 2021/0008373 A1 | 1/2021 | Single et al. | |

* cited by examiner

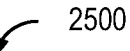

2500

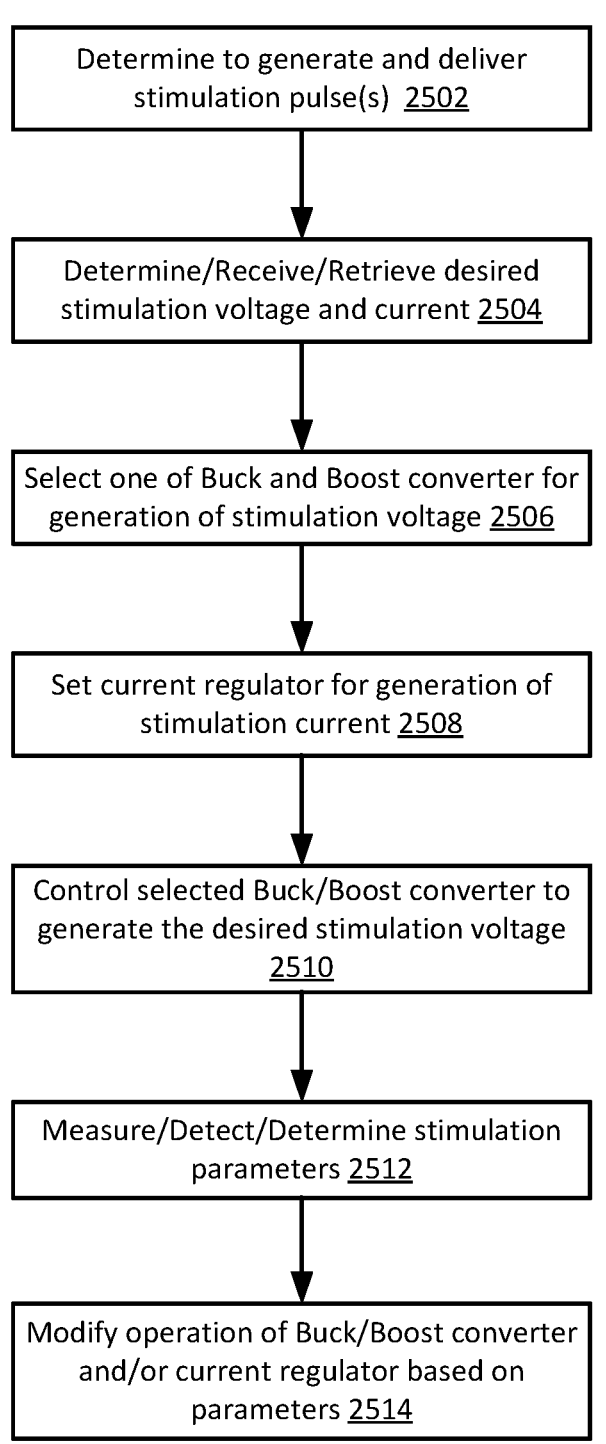

Determine to generate and deliver stimulation pulse(s)  2502

Determine/Receive/Retrieve desired stimulation voltage and current 2504

Select one of Buck and Boost converter for generation of stimulation voltage 2506

Set current regulator for generation of stimulation current 2508

Control selected Buck/Boost converter to generate the desired stimulation voltage 2510

Measure/Detect/Determine stimulation parameters 2512

Modify operation of Buck/Boost converter and/or current regulator based on parameters 2514

FIG. 9

ENERGY EFFICIENT ELECTRICAL PULSE GENERATING DEVICE

BACKGROUND

This application relates to electrical pulse generating systems and associated devices, methods of treatment related to these electrical pulse generating systems, and the implantation and configuration of such treatment systems.

Sacral Neuromodulation (SNM) is an established therapy that provides a safe, effective, reversible, and long-lasting treatment option for the management of urinary urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG), also referred to herein as an "implantable neurostimulator" or a "neurostimulator." SNM has also been approved to treat chronic fecal incontinence in patients who have failed or are not candidates for more conservative treatments.

Treatments with implantable neurostimulation systems have become increasingly common in recent years. While such systems have shown promise in treating a number of conditions, effectiveness of treatment may vary considerably between patients. A number of factors may lead to the very different patient outcomes, and viability of treatment can be difficult to determine before implantation. For example, stimulation systems often make use of an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues.

However, operation of an IPG may be challenging for many patients. These challenges include the challenges associated with recharging the IPG and/or maintaining a sufficient level of charge in the IPG. For example, some patients may struggle with properly positioning a charging device with respect to the IPG to enable successful recharging.

While recharging of an IPG may be complicated, currently non-rechargeable IPGs have a limited useful life. When the battery dies in a non-rechargeable IPG, the only path to further stimulation lies in explanting the old IPG and replacing it with a new IPG every few years. This requires additional surgical procedures, adds to patient discomfort, and results in significant costs to healthcare systems. Thus, neither current rechargeable IPGs nor current non-rechargeable IPGs provide ideal treatment solutions.

The tremendous benefits of these neural stimulation therapies have not yet been fully realized. Therefore, it is desirable to provide improved neurostimulation methods, systems and devices, as well as methods for implanting and configuring such neurostimulation systems for a particular patient or condition being treated. It would be particularly helpful to provide such systems and methods with improved energy efficiency in order to reduce or eliminate the requirement for recharging an implantable device.

SUMMARY

Exemplary embodiments of an IPG are described below. The IPG is configured to stimulate a nerve of a human body.

The various embodiments described herein include various systems, methods, and circuitry for improving the energy efficiency of an IPG, and thereby decreasing the power consumption of the IPG. In the context of rechargeable IPGs, this increased efficiency decreases the frequency of recharging the IPG. For non-rechargeable IPGs, the increased efficiency increases the useful life of the IPG because the internal power supply (e.g., a battery) will have a longer life. The improved design of the various embodiments described herein allows for the achievement of an increase in the useful life without increasing the size of the power supply (e.g., battery).

As described herein, the energy efficiency of the IPG may be increased due to several innovative features associated with the design and operation of the IPG. For example, the energy efficiency may be increased due to the innovative design of the electrical circuitry used by the IPG to generate the stimulation pulses. The electrical circuitry may include several features, any of which may be implemented together or separately, that result in increased efficiency and lower power consumption of the IPG. Also, during operation of the IPG, the stimulation pulses delivered in a more efficient manner to thereby lower the power consumption of the device.

The electrical circuitry includes several different features which improve the energy efficiency of the IPG. One of these features is related to the voltage converter for generating the stimulation pulse. Another feature that may be implemented for reducing the power demand and increasing the efficiency of the IPG is the innovative current source (or regulator) described below. The IPG also includes an innovative feedback feature that is implemented through electronics and functions to increase the energy efficiency of the IPG by lowering the power requirements. The IPG may utilize any known current source circuits compatible with the IPG as described herein. However, for certain exemplary embodiments described below, a preferred current regulator is described.

The neurostimulation device may include a series capacitor configured to be charged during the first phase of the stimulation current and discharged during the second phase of the stimulation current. The energy stored in the capacitor during the first phase of the stimulation current is used to generate the stimulation current during the second phase thereby reducing the energy withdrawn from the energy source. The circuit may include a switch configured to selectively couple the series capacitor to the converter during the first phase. The capacitor is configured to be decoupled from the converter during the second phase so that the stored energy in the capacitor can be used to generate the second phase of the stimulation current thereby reducing the energy withdrawn from the energy source.

The IPG may utilize any known controller configured to communicate with the circuits described herein. For example, a processor, a digital register, a dedicated circuitry, or logic that is permanently configured (e.g., as a special-purpose processor, such as a field programmable gate array (FPGA) or an application-specific integrated circuit (ASIC)) to perform certain operations. For the exemplary embodiment(s) described below, an exemplary processor is utilized.

Several of the features contributing to the energy efficiency of the neurostimulator device are generally described below with regard to the disclosed embodiments.

For example, the present application includes a disclosure of an energy efficient device for delivering one or more electrical pulses to a target region within a patient's body. The device includes a housing with a controller and an energy storage device both located in the housing. A stimulation circuit is also located in the housing. The stimulation circuit generates a stimulation current that provides the one or more electrical pulses and includes a converter for generating the stimulation current and a current source. The converter includes a voltage increasing circuit and a voltage reducing circuit. The energy storage device may be configured to provide a base voltage to the stimulation circuit. The controller may be configured to control the converter to adjust the base voltage downwardly based on a feedback signal from the current source thereby reducing the power withdrawn from the energy storage device and extending the operational life of the neurostimulator.

According to another disclosed embodiment, an energy efficient implantable neurostimulator for delivering one or more electrical pulses to a target region within a patient's body is provided. The neurostimulator includes a housing, a controller located in the housing and an energy source located in the housing. The neurostimulator also includes a stimulation circuit that generates a stimulation current that provides the one or more electrical pulses. The stimulation circuit includes a converter for generating the stimulation current, wherein the voltage converter includes a voltage increasing circuit and a voltage reducing circuit. The stimulation circuit also includes feedback electronics including a feedback signal circuit that generates a feedback signal based on the stimulation current, wherein the feedback signal is delivered to the converter and the controller.

According to another disclosed embodiment, an implantable neurostimulator is provided. The neurostimulator includes a stimulation circuit located in the housing, wherein the stimulation circuit generates a stimulation current having a first phase and a second phase, wherein the stimulation current provides the one or more electrical pulses. The stimulation circuit includes a converter, a current source and a feedback signal circuit. The converter includes a voltage increasing circuit and a voltage reducing circuit. The feedback signal circuit generates a feedback signal based on the stimulation current, wherein the feedback signal is delivered to the converter and the controller. A controller may be configured to control the converter to adjust the base voltage downwardly only during the first phase depending on the feedback signal received thereby reducing the power withdrawn from the energy source and extending the operational life of the neurostimulator.

According to another disclosed embodiment an energy efficient device for delivering one or more electrical pulses to a target region within a patient's body is disclosed. The device includes a current source that includes a pair of cascode arranged transistors that are controlled to maintain an amplitude of the stimulation current substantially constant. A controller is provided to control the stimulation circuit to minimize the voltage across one of the pair of cascode arranged transistors in order to reduce the amount of energy withdrawn from the energy source while the current source operates to provide the substantially constant stimulation current. The device may be configured so that a stimulation current includes a set of phases including at least a first phase and a second phase. The current source may include a set of current sources corresponding to each phase in the set of phases including at least a phase one current source and a phase two current source. The current sources may each include a pair of cascode arranged transistors.

According to another disclosed embodiment, an implantable neurostimulator is provided. The neurostimulator includes a stimulation circuit that is configured to provide the stimulation current in at least a first phase and a second phase. The neurostimulator also includes a current source that includes a first pair of cascode arranged transistors operative during the first phase and second pair of cascode arranged transistors operative during the second phase. The neurostimulator is configured so that a voltage of one of the first and second pair of cascade transistors is monitored by the controller in order to reduce the amount of energy withdrawn from the energy storage device while the current is being regulated to provide a substantially constant stimulation current. According to another embodiment, a controller is configured to maintain an amplitude of the stimulation current substantially constant. The controller also may be configured to control the pair of cascode transistors to minimize the voltage across one of the pair of cascode arranged transistors in order to reduce the amount of energy withdrawn from the energy storage device while the current source operates to provide the substantially constant stimulation current.

According to another disclosed embodiment of an implantable neurostimulator, a current source includes a first phase current source and a second phase current source, wherein the first phase current source includes a first transistor that is controlled to maintain an amplitude of the stimulation current substantially constant. A second transistor may be provided and a controller may be utilized to minimize the voltage across the first transistor in order to reduce the amount of energy withdrawn from the energy storage device while the current source operates to provide the substantially constant stimulation current. In an alternative embodiment, the first transistor may be part of a current mirror.

According to another disclosed embodiment, an energy efficient device for delivering an electrical pulse to a target region within a patient's body is provided, and the device includes a stimulation circuit that includes an analog switch. The device is configured so that analog switch is powered by a switch power supply, and wherein an output voltage of the switch power supply is greater than the stimulation voltage generated by the stimulation circuit. The power supply may be configured as a bias voltage power supply. Alternatively, the power supply may be a charge pump. In addition, the device may include a voltage converter that includes both a voltage increasing circuit and a voltage reducing circuit.

According to another disclosed embodiment, an implantable neurostimulation device is provided. The device includes a stimulation circuit that includes a converter for generating a stimulation voltage that drives the electrical pulse. The stimulation circuit includes a selecting circuit with a selector switch for controlling the output of the converter. The stimulation circuit includes a level shifter for operating the selector switch. The selecting circuit may be powered by a bias voltage power supply. In addition, the level shifter may also be powered by the bias voltage power supply to supply an output voltage of the bias voltage power supply to the selecting circuit. The selecting circuit may also include a first selector switch coupled to a voltage increasing circuit of the converter and operated by a first level shifter, and a second selector switch coupled to a voltage decreasing circuit of the converter and operated by a second level shifter. According to a disclosed embodiment, the device may be configured so that a bias voltage power supply is powered by the energy storage device and provides an output voltage for powering the selecting circuit. The output voltage may be independent of the stimulation voltage; thereby allowing the stimulation voltage to be decreased in order to reduce the energy withdrawn from the energy source.

A more detailed description of the structure and operation of the components of the energy efficient neurostimulator device is set forth below. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIG. 9 shows a flowchart illustrating one embodiment of a process for high-level control of an IPG for delivering a stimulation pulse with the IPG.

DETAILED DESCRIPTION

Figure 1:
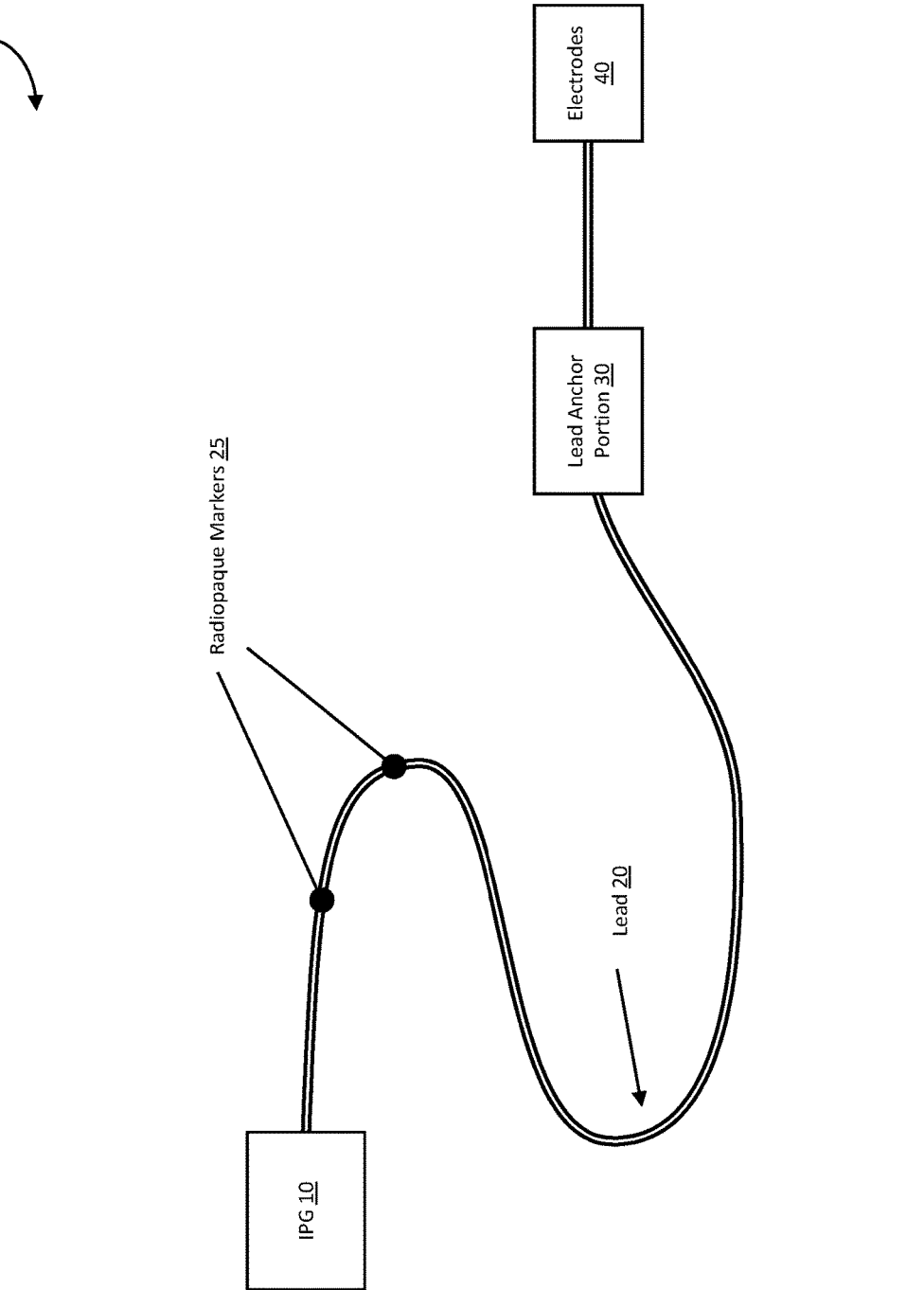
FIG. 1 shows an example of a neurostimulation system having an implantable stimulation lead and an implantable pulse generator.

The present application relates to pulse generating devices (e.g., implantable pulse generators) and treatment systems for a patient. These systems may include implantable devices that generate pulses for treating various conditions. As an example, the present application relates to neuro-stimulation treatment systems and associated devices, as well as methods of treatment, implantation/placement and configuration of such treatment systems. In one embodiment, at least one sacral nerve stimulation treatment system configured to treat overactive bladder ("OAB") and relieve symptoms of bladder related dysfunction is disclosed. However, the devices and systems disclosed herein may also be utilized for a variety of neuromodulation uses, such as fecal dysfunction, and for the treatment of pain or other indications, such as movement or affective disorders.

Neurostimulation (or neuromodulation as may be used interchangeably hereunder) treatment systems, such as any of those described herein, can be used to treat a variety of ailments and associated symptoms, such as acute pain disorders, movement disorders, and affective disorders, as well as bladder related dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include but are not limited to muscle paralysis, tremor, dystonia and Parkinson's disease. Affective disorders include but are not limited to depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and/or urgency-frequency. Urge incontinence is the involuntary loss of urine associated with a sudden, strong desire to void (urgency). Urgency-frequency is the frequent, often uncontrollable urge to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

The methods and systems described herein are particularly suited for treatment of urinary and fecal dysfunctions. These dysfunctions have been historically under-recognized and significantly underserved by the medical community. OAB is one of the most common urinary dysfunctions in the community. It is a complex condition characterized by the presence of bothersome urinary symptoms, including urgency, frequency, nocturia, and urge incontinence.

SNM is an established therapy that provides a safe, effective, reversible and long-lasting treatment option for the management of urinary urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG), also referred to herein as an "implantable neurostimulator" or a "neurostimulator." The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed other treatments or are not candidates for more conservative treatments.

FIG. 1 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead 20. The lead 20 includes a lead anchor portion 30 with a series of tines extending radially outward so as to anchor the lead 20 and maintain a position of the neurostimulation lead 20 after implantation. The lead 20 may further include one or more radiopaque markers 25 to assist in locating and positioning the lead using visualization techniques such as fluoroscopy. In some embodiments, the IPG 10 provides monopolar or bipolar electrical pulses that are delivered to the targeted nerves through one or more neurostimulation electrodes 40, typically four electrodes. In sacral nerve stimulation, the lead 20 is typically implanted through the S3 foramen as described herein.

The system may further include a patient remote and clinician programmer, each configured to wirelessly communicate with the implanted IPG 10. The clinician programmer may be a tablet computer used by the clinician to program the IPG 10. The patient remote may be a battery-operated, portable device that utilizes radio-frequency (RF) signals to communicate with the IPG 10 and allows the patient to adjust the stimulation levels, check the status of the IPG battery level, and/or to turn the stimulation on or off. One or more properties of the electrical pulses may be controlled via a controller of the IPG 10. In some embodiments, these properties may include, for example, the frequency, strength, pattern, duration, or other aspects of the timing and magnitude of the electrical pulses. These properties may further include, for example, a voltage, a current, or the like. This control of the electrical pulses may include the creation of one or more electrical pulse programs, plans, or patterns, and in some embodiments, this may include the selection of one or more pre-existing electrical pulse programs, plans, or patterns. In one aspect, the IPG 10 includes a controller, also referred to herein as a processor or microprocessor, having one or more pulse programs, plans, or patterns that may be created and/or pre-programmed. In some embodiments, the IPG 10 may be programmed to vary stimulation parameters including varying pulse amplitude within a range from 0 mA to 10 mA, varying pulse width within a range from 50 us to 500 μs, varying pulse frequency within a range from 5 Hz to 250 Hz, switching between stimulation modes (e.g., continuous or cycling), and selecting an electrode configuration (e.g., anode, cathode, or off), to achieve the optimal therapeutic outcome specific to the patient. In particular, this allows for an optimal setting to be determined for each patient even though the optimal setting for each parameter may vary from person to person.

Figure 2:
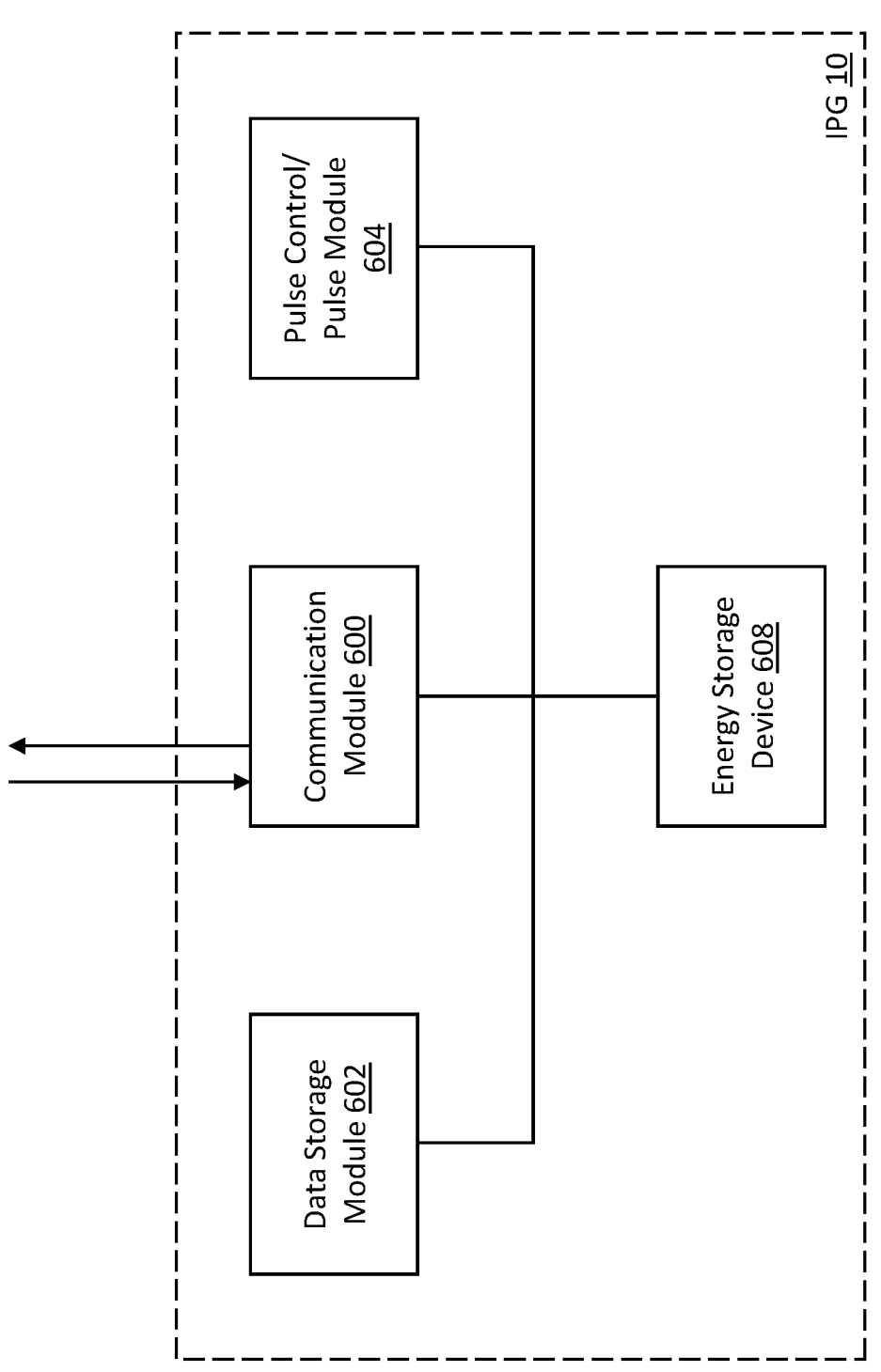
FIG. 2 shows a high-level schematic illustration of one embodiment of the architecture of an IPG.

FIG. 2 shows a high-level schematic illustration of one embodiment of the architecture of the IPG 10. In some embodiments, each of the components of the architecture of the IPG 10 may be implemented using the processor, memory, and/or other hardware components of the IPG 10. In some embodiments, the components of the architecture of the IPG 10 may include software that interacts with the hardware of the IPG 10 to achieve a desired outcome, and the components of the architecture of the IPG 10 may be located within the housing.

In some embodiments, the IPG 10 may include, for example, a communication module 600. The communication module 600 may be configured to send data to and receive data from other components and/or devices of the exemplary nerve stimulation system including, for example, the clinician programmer 60 and/or the patient remote 70. In some embodiments, the communication module 600 may include one or several antennas and software configured to control the one or several antennas to send information to and receive information from one or several of the other components of the IPG 10.

In some embodiments, the communication module 600 may be configured to operate in a plurality of modes, which may include (but are not limited to) a detect mode, a receive mode, and a data transfer mode. In one embodiment, the communication module 600 may operate in detect mode by transmitting a detection burst. In one embodiment, this detection burst may be followed by a sleep period. In one embodiment, the detection burst may be included in a plurality of detection bursts, wherein the plurality of detection bursts is configured to provide detection bursts across a frequency spectrum. In one embodiment, the communication module 600 may operate in receive mode by confirming a detection of a communication channel, identifying the communication channel, and locking the preamble for subsequent data communications with the communication channel. The communication channel may be a communication channel between the communication module 600 and other components of the IPG 10, or between the communication module 600 and outside devices such as the clinician programmer 60 and/or the patient remote 70. In one embodiment, the communication module 600 may operate in data transfer mode by using at least one ON-period to receive discreet packets of data across the communication channel. The at least one ON-period may be interspersed with periodic reception bursts to ensure synchronization with the other end of the communication channel.

The IPG 10 may further include a data module 602. The data module 602 may be configured to manage data relating to the identity and properties of the IPG 10. In some embodiments, the data module 602 may include one or several databases that may, for example, include information relating to the IPG 10 such as, for example, the identification of the IPG 10, one or several properties of the IPG 10, or the like. In one embodiment, the data identifying the IPG 10 may include, for example, a serial number of the IPG 10 and/or other identifiers of the IPG 10 including, for example, a unique identifier of the IPG 10. In some embodiments, the information associated with the property of the IPG 10 may include, for example, data identifying the function of the IPG 10, data identifying the power consumption of the IPG 10, data identifying the charge capacity of the IPG 10 and/or power storage capacity of the IPG 10, data identifying potential and/or maximum rates of charging of the IPG 10, and/or the like.

The IPG 10 may include a pulse control 604. In some embodiments, the pulse control 604 may be configured to control the generation of one or several pulses by the IPG 10. In some embodiments, for example, this may be performed based on information that identifies one or several pulse patterns, programs, or the like. This information may further specify, for example, the frequency of pulses generated by the IPG 10, the duration of pulses generated by the IPG 10, the strength and/or magnitude of pulses generated by the IPG 10, or any other details relating to the creation of one or several pulses by the IPG 10. In some embodiments, this information may specify aspects of a pulse pattern and/or pulse program, such as, for example, the duration of the pulse pattern and/or pulse program, and/or the like. In some embodiments, information relating to and/or for controlling the pulse generation of the IPG 10 may be stored within the memory.

In some embodiments, the pulse module 604 may include stimulation circuitry. The stimulation circuitry may be configured to generate and deliver one or several stimulation pulses, and specifically may be configured to generate a voltage driving a current forming one or several stimulation pulses. This circuitry may include one or several different components that may be controlled to generate the one or several stimulation pulses, to control the one or several stimulation pulses, and/or to deliver the one or several stimulation pulses.

The IPG 10 may include an energy source, such as an energy storage device 608. The energy storage device 608, which may include the energy storage features, may be any device configured to store energy and may include, for example, one or several batteries, capacitors, fuel cells, or the like.

Figure 3:
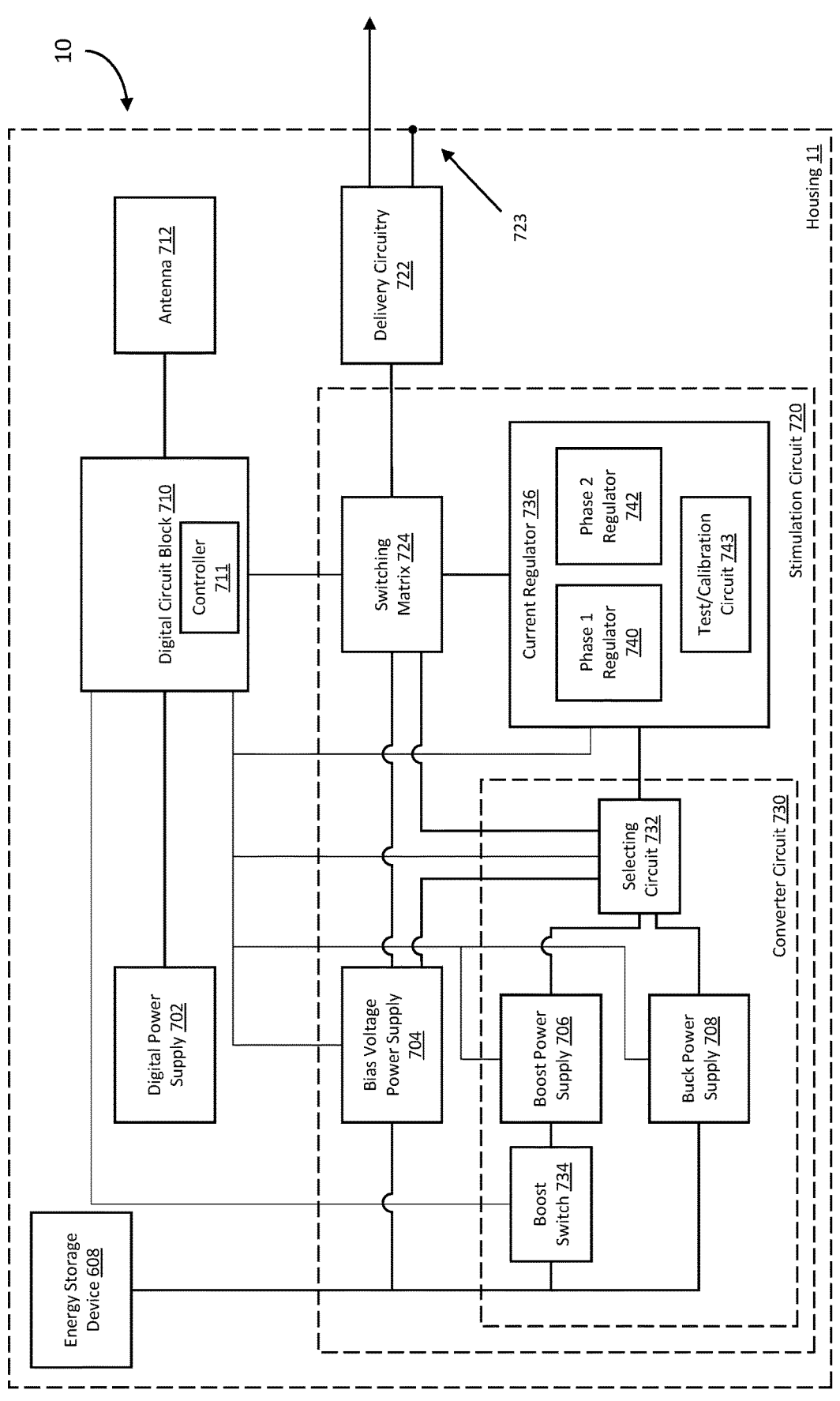
FIG. 3 shows a high-level schematic illustration of another embodiment of the architecture of an IPG.

FIG. 3 is a high-level schematic illustration of another embodiment of the architecture of the IPG 10. In some embodiments, the components shown in the high-level schematic illustrations of FIGS. 2 and 3 may be distinct and separate components, and in some embodiments, the components shown in the high-level schematic illustrations of FIGS. 2 and 3 may operate together in an integrated system. For example, certain components shown in the high-level schematic of FIG. 3 may be included in the modules of FIG. 2.

In some embodiments, each of the components of the architecture of the IPG 10 may be implemented using the processor, memory, and/or other hardware components of the IPG 10. In some embodiments, the components of the architecture of the IPG 10 may include software that interacts with the hardware of the IPG 10 to achieve a desired outcome, and the components of the architecture of the IPG 10 may be located within the housing.

The IPG 10 may include an energy storage device 608, which may provide power to a plurality of power supplies 702, 704, 706, 708. In some embodiments, the energy storage device 608 may be directly coupled to one or more of these power supplies 702, 704, 706, 708, and thus the energy storage device 608 may directly power one or more of these power supplies 702, 704, 706, 708. In some embodiments, the energy storage device 608 may comprise a battery.

As shown in FIG. 3, the IPG 10 includes an energy storage device 608 (e.g., a battery) and electrodes 722. The IPG 10 includes a digital circuit block 710, which in turn includes a processor configured to control the voltage converter. The stimulation circuit 720 may include a bias voltage power supply 704, a current regulator or current source 736, stimulation or converter circuitry 730, and a switching matrix 724. The converter circuitry 730 includes a boost switch 734, Boost Power Supply 706, Buck Power Supply 708, and a selecting circuit or selecting circuit 732.

The IPG 10 includes a digital power supply 702. The digital power supply 702 may provide power to the digital circuit block 710. In some embodiments, the digital circuit block 710 may be configured to operate with a low voltage. In some embodiments, for example, this may include the digital circuit block 710 being configured to operate at a lower voltage to thereby increase efficiency of the digital circuit block 710. In some embodiments, the digital power supply 702 may be configured to provide power at a voltage level at which the digital circuit block 710 operates. This may include, for example, a voltage less than 2.5V, less than 2V, between 1V and 2V, approximately 1.8V, or any other or intermediate voltage.

A buck mode switching regulator may efficiently convert a battery voltage to a lower voltage (e.g., 1.8V) for use by a controller or processor and other low voltage components. A protection fuse may be employed. The low voltage power supply may be turned off during a system watch dog fault reset cycle. The low voltage power supply may include an output discharge to assure that powered components have their power completely removed during a watch dog reset cycle.

The digital circuit block 710 may include one or several components including, for example, one or several sensors, a watchdog, a timer, a transceiver and/or radio, one or several processors 711, or the like. In some embodiments, these one or several sensors may comprise one or several temperature and/or humidity sensors. The one or several processors 711 may include, for example, a CPU, and the one or several processors 711 may control operation of one or several aspects of the IPG 10, including one or several of the modules shown in FIG. 6 and/or FIG. 7.

The digital circuit block 710 may include a radio and/or transceiver which may communicate with other components of the nerve stimulation system including, for example, the clinician programmer 60 and/or the patient remote 70. In some embodiments, the radio and/or transceiver may communicate with these other components of the nerve stimulation system via, for example, an antenna 712, which may be, in some embodiments, located in the header 11 of the IPG 10.

The processor CPU may be a standalone embedded microcontroller with on-chip program memory, RAM, CPU related peripherals and analog and digital I/O ports. In one embodiment, all device operations are orchestrated by software running in the CPU. A two-way radio may be provided. The radio may be a complete radio on chip, needing only a filtered power supply, a crystal frequency reference, and an RF matching circuitry to couple the radio differential RF connection to a PCB routed transmission line (e.g., 50-ohm line). The radio power supply is enabled by the CPU via controllable power switch. The CPU may communicate digital data to and from the radio via an SPI serial interface. An accurate micro-power oscillator (e.g., 32.768 KHz) provides a reference time base to the CPU. A system watchdog may be employed to cycle the low voltage power if the CPU does not pulse the watchdog approximately every three minutes. A temperature and humidity sensor may be employed, wherein the temperature and humidity sensor is read by the CPU via an I2C serial interface. The sensor is powered by the same power switch as the radio. An analog switch that enables reading of the battery voltage by the CPU is provided.

The processor 711 of the digital circuit block 710 may select one of a voltage reducing circuit such as a buck converter 708 and a voltage increasing circuit such as a boost converter 706 for generation of at least part of the stimulation pulse. The voltage reducing circuit may include, for example, a buck converter or a step-down transformer. The voltage increasing circuit may include, for example, a step-up transformer or a boost converter. This control may direct the selecting circuit 732 to select the desired one of the buck converter 708 and the boost converter 706 for generation of the stimulation pulse and/or of at least a part of the stimulation pulse such as all or portions of a first phase of the stimulation pulse. The selecting circuit 732 may be directed to choosing the converter that will provide more efficient use of the power withdrawn from the energy storage device 608 for a given moment. The employment of a voltage decreasing circuit permits the power withdrawn from the energy storage device 608 to be reduced and allows for the operational life of the neurostimulator to be extended.

The IPG 10 may include a stimulation circuit 720. The stimulation circuitry 720 may generate one or several simulation pulses and/or may provide these one or several stimulation pulses to the delivery circuitry and/or to the electrodes 722. The stimulation circuitry 720 may include a bias voltage power supply 704. The bias voltage power supply 704 may be powered by the energy storage device 608 and may power one or several switches in the IPG 10. In some embodiments, the bias voltage power supply 704 may output a voltage greater than a voltage of the stimulation pulses. In some embodiments, the bias voltage power supply 704 may output a voltage higher than a voltage of the energy storage device 608. In some embodiments, the bias voltage power supply 704 may comprise a voltage increasing supply that provides voltage higher than the voltage of the energy storage device 608, which may be a battery. In some embodiments, the bias voltage power supply 704 may comprise a charge pump, a fly back power supply, a step up transformer, a voltage multiplier, or the like. The output voltage of the bias voltage power supply 704 is independent of the stimulation voltage, thereby allowing the stimulation voltage to be decreased in order to reduce the energy withdrawn from the energy source.

Figure 8:
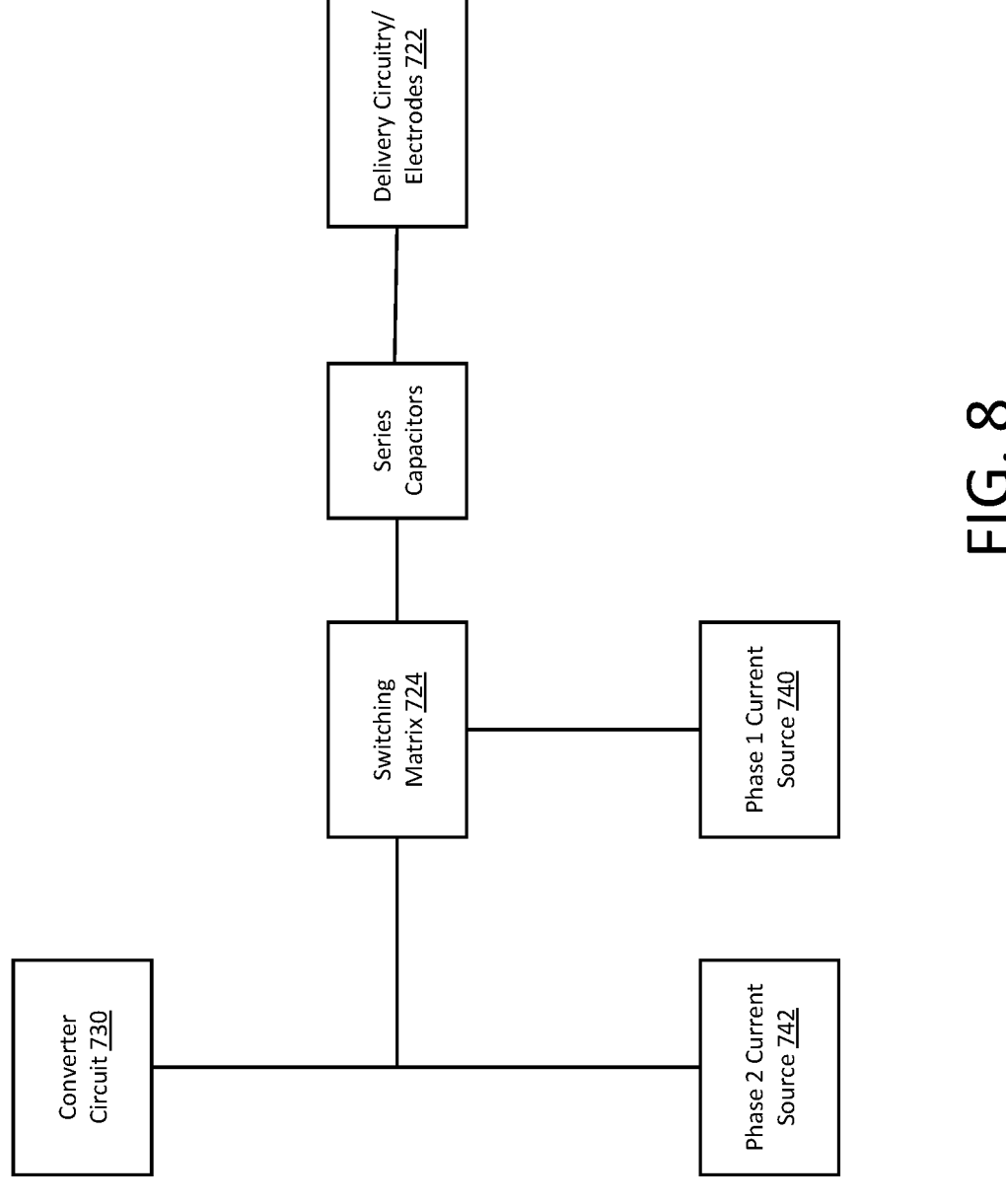
FIG. 8 is a high-level schematic showing the major components of an IPG including the current regulator.

The switching matrix 724 may comprise a plurality of switches, wherein the plurality of switches may couple circuitry, components of the IPG 10 or of the stimulation circuitry 720, and/or modules to each other and/or to the delivery circuitry and/or electrodes 722. As shown in FIG. 8, the IPG 10 may include series capacitors which may be considered separate or part of the delivery circuitry 722.

The IPG 10, and specifically the stimulation circuit 720 may include converter circuitry 730, also referred to herein as a stimulation circuitry 730. The converter circuitry 730 may be configured to generate a voltage, referred to herein as a stimulation driving voltage or a stimulation voltage, which may be coupled to the delivery circuitry and/or to the electrodes 722. The stimulation voltage may drive the stimulation current.

In some embodiments, the stimulation pulse may be segmented into a set of phases including at least a first phase and a second phase (or alternatively, a first phase and a following phase). While this disclosure is generally directed towards a two-phase structure, it should be understood that the methods and systems disclosed herein may be applied to the generation of a stimulation pulse with more than two phases or to a device configured to generate such a stimulation pulse. For example, while this disclosure generally focuses on the first phase as a capacitor charging phase and the second phase as a capacitor discharging phase, the "following phase" may be any phase in the set of phases of the stimulation current where the capacitor holds a residual charge, including multiple phases following the first phase if necessary. As such, the second phase may alternatively be described as a following phase or a final phase of the set of phases of the stimulation pulse.

In some embodiments, the switching matrix 724 may include one or several switching arrays coupled to, for example, the one or several stimulation switches. In some embodiments, the one or several switching arrays may determine a routing of stimulation pulses generated by the stimulation or converter circuitry 730 and the one or several stimulation switches. In some embodiments, these one or several switching arrays may, for example, couple the output of the one or several stimulation switches with one or several electrodes and/or delivery circuitry 722, and/or coupled the output of the one or several stimulation switches with a test load of a test/calibration circuit. In some embodiments, this coupling may be directed to designating circuitry and/or electrodes to act as anodic and/or cathodic channels. In some exemplary embodiments the one or several switching arrays may not be modified during the phases of the stimulation pulse delivery, but are instead modified during the changing of selected electrodes for stimulation pulse delivery or for testing/calibration.

In one embodiment, the delivery circuitry 722 includes a connection to the housing of the IPG 10 such that the housing connection may serve as an anode in the same capacity as an electrode that is configured to function as an anode.

The converter circuitry 730 may include, in some embodiments, a buck converter and/or a boost converter. In some embodiments, each of the buck converter and the boost converter may include a power supply, thus, the buck converter may include the buck power supply 708, and the boost converter may include the boost power supply 706. Each of the buck and the boost power supplies 706, 708 are independently coupled to the energy storage device 608, and may receive power from the energy storage device 608. Each of the buck and boost converter may use this power in the generation of one or several stimulation pulses, and specifically may use this power in the generation of at least a part of one or several stimulation pulses. In some embodiments, the generation of one or several stimulation pulses by one of the buck and boost converter includes the generation of the stimulation voltage by the one of the buck and boost converter. In some embodiments, for example, each of the buck and boost converter may be configured to generate all or portions of phase one of the stimulation pulse, and specifically may be configured to generate a stimulation voltage driving a stimulation pulse during all or portions of phase one of the stimulation pulse, and specifically driving a stimulation current during all or portions of phase one of the stimulation pulse.

In some embodiments, the boost converter, and specifically the boost power supply 706 may be selectively powered, and in some embodiments, the buck converter, and specifically the buck power supply 708 may be constantly powered. The buck converter may have an extremely low current shutdown mode that is operated by the controller or processor and, as a result, the buck converter may always be connected or coupled to the energy source or battery.

In some embodiments, for example, the boost power supply 706 is switchably coupled with the energy storage device 608 via boost switch 734, or in other words, the boost switch 734 selectably couples the boost power supply 706 to the energy storage device 608.

The boost switch 734 is coupled with the digital circuit block 710 and, thus, may be controlled by the processor 711 in the digital circuit block 710. In some embodiments, for example, when the processor 711 of the digital circuit block 710 controls the boost power supply 706 to generate all or portions of the stimulation pulse, the processor 711 may be configured to close the boost switch 734 and/or control the boost switch 734 to close. In some embodiments, for example, when the processor of the digital circuit block 710 controls the boost power supply 706 to not generate all or a portion of the stimulation pulse, such as, for example, when no stimulation pulse is generated or when a portion of the stimulation pulse is generated by the buck converter, the processor of the digital circuit block 710 may be configured to open the boost switch 734 and/or control the boost switch 734 to open. Thus, in some embodiments in which the boost converter is not generating and/or delivering a stimulation pulse, the switch 734 may be opened by the processor 711 of the digital circuit block 710.

The boost converter supply 706 may be configured for fast turn-on. In contrast, the buck converter supply 708, which may be constantly powered, may be configured for slow turn-on. Specifically, as the boost converter supply 706 is selectively powered, fast turn-on may be important for the boost converter supply, whereas, as the buck converter supply 708 is constantly powered, the buck converter 708 may be configured for fast turn-on or slow turn-on.

In some embodiments, the converter circuitry 730 may further include a selecting circuit 732. In some embodiments, the selecting circuit 732 may select and couple one of the buck converter and the boost converter, directly or indirectly, to the delivery circuitry and/or the electrodes 722. In some embodiments, this may include an indirect connection via the switching matrix 724.

The selecting circuit 732 may comprise a plurality of switches. These switches may include, for example, one or several switches, and specifically, one or several analog switches. In some embodiments, a plurality of analog switches couple at least a portion of the stimulation circuitry 730 of the implantable neurostimulator to at least one electrode direct, or indirectly via, for example, the switching matrix 724. In some embodiments, the plurality of switches may include at least one level shifter and at least one stimulation switch. The at least one level shifter may, in some embodiments, maintain a voltage applied to the at least one stimulation switch at one of a finite number of predetermined voltages. In some embodiments, this finite number of predetermined voltages may include a first voltage and a second voltage. The first voltage may, in some embodiments, be zero volts or a ground voltage, and the second voltage may, in some embodiments, be a voltage output of the bias voltage power supply 704.

In some embodiments, the selecting circuit may comprise an analog circuit configured to select one of the buck converter and the boost converter for generation of the stimulation pulse. The selecting circuit 732 may be controlled by the digital circuit block 710, and specifically by the processor 711 of the digital circuit block 710. Thus, in some embodiments, the processor 711 may, as a part of generating a stimulation pulse, selecting one of the buck converter and the boost converter, and may control the selecting circuit 732 based on this selection.

The IPG 10 may include a current source or current regulator 736. The current source 736 may be configured to regulate a current of the stimulation pulse. The current regulator may be a current source, or a current sink which may control the amplitude of a current of the stimulation pulse. In some embodiments, the current regulator may be described as a bidirectional current source. In some embodiments, the current source 736 may be located in a return line of the IPG 10, or may form part of a return line of the IPG 10. The return line is a voltage signal line that is utilized by the processor 711 in order to control the DAC of the second signal portion 824. An array of resistors may form a "power of two" DAC which may be employed to fine tune the feedback signal from the phase one current source cascode to optimize power usage. In one embodiment, the processor 711 uses a lookup table to provide control signals to set an output of the DAC.

The return line may be the output of the current source 736. The current source 736 may include one or more devices having variable conductance controlled by an input node and/or current flow controlled by an input node. The input node, also referred to herein as a control input, may include a gate of, for example, a transistor such as a field-effect transistor. The current source may comprise, in some embodiments, one or more sets of cascode arranged transistors, also referred to herein as transistors in cascode arrangement. In some embodiments, a set of cascode arranged transistors may comprise a pair of transistors in a cascode arrangement. These transistors may, in some embodiments, comprise field-effect transistors (FETs) such as metal-oxide-semiconductor field-effect transistors (MOSFETs: N-channel/P-channel). In some embodiments in which the current source comprises a set of cascode arranged transistors, the current allowed through the set of cascode arranged transistors may be controlled by a voltage applied to a control input, such as a gate, of at least one transistor of the set of cascode arranged transistors. In some embodiments, this control may include directing at least one of the components of the current source 736 to act as a current source or a current sink as necessary.

In some embodiments, the current source 736 may further include a voltage holding capacitor, also referred to herein as a regulation capacitor, coupled to the control input of the at least one of the set of cascode arranged transistors. In some embodiments, the voltage holding capacitor may be directly coupled to the control input of the at least one of the set of cascode arranged transistors, and in some embodiments, the voltage holding capacitor may be coupled to the control input of the at least one of the set of cascode arranged transistors via one or several switches. In some embodiments, the voltage holding capacitor may be charged to a voltage, and the voltage of the voltage holding capacitor may be applied to the control input of the at least one of the set of cascode arranged transistors. In some embodiments, the voltage of the voltage holding capacitor is applied to the control input of the at least one of the set of cascode arranged transistors to thereby control the current allowed through the cascode arranged transistors.

In some embodiments, the current source 736 may comprise a phase one regulator or current source 740 and a phase two regulator or current source 742. In some embodiments, the phase one current source 740 may be configured to regulate a first current of the stimulation pulse during a first phase of the simulation pulse, and in some embodiments, the phase two current regulator or current source 742 may be configured to regulate a second current of the stimulation pulse during a second phase of the stimulation pulse. The first phase is a first stimulation signal configured to stimulate the patient's nerve at a first current. The second phase is a second stimulation signal configured to stimulate the patient's nerve at a second current. The first current and the second current may be in a direction opposite of the first current. The phase one current source 740 or the phase two current source 742 may be set to act as a current source or current sink depending on the phase of the stimulation pulse. The second phase may also occur after some set period of time (e.g. interphase delay).

In general, according to one embodiment, the phase one and phase two pulldown current sources are each made up of two N-Channel MOSFETs wired in a cascode configuration with the lower source pin connected through a resistor to ground. The cascode circuit provides a voltage compliant pull down constant current source out the upper drain pin, by having a fixed DC voltage applied to the lower gate. The high gain of the MOSFET causes the drain voltage to remain a minimally variant voltage difference from the gate to the source and through the source resistor to ground. With gate current being practically zero, the upper MOSFET drain current is equal to the lower MOSFET source current which is equal to lower source voltage divided by the source resistor. A cascode configuration is used to minimize the voltage change of the lower drain, and hence minimize shift in current due to changes in voltage across the lower MOSFET. The voltage across the lower MOSFET may be minimized in order to reduce the amount of energy withdrawn from the energy source while the current source operates to provide a substantially constant stimulation current.

In some embodiments, the phase one current source 740 may comprise a first set of cascode arranged transistors and the phase two current source 742 may comprise a second set of cascode arranged transistors. In some embodiments, a voltage applied to a control input of at least one of the transistors in the first set of cascode arranged transistors may regulate the first current of the stimulation pulse during the first phase, and a voltage applied to a control input of at least one of the transistors in the second set of cascode arranged transistors may regulate the second current of the stimulation pulse during the second phase.

During phase two, the cascode transistors associated with phase one operate with a negative current applied into the top drain, hence collapsing the voltage across the cascode pair and causing both MOSFETs to be fully on and effectively grounding the phase one pull down current source node. The cascode transistors associated with phase two operate in current regulation mode until there is insufficient voltage to achieve the target phase two current, thereby collapsing the voltage across the pair of phase two cascode transistors and turning the cascode transistors fully on for the remainder of phase two.

Figure 4:
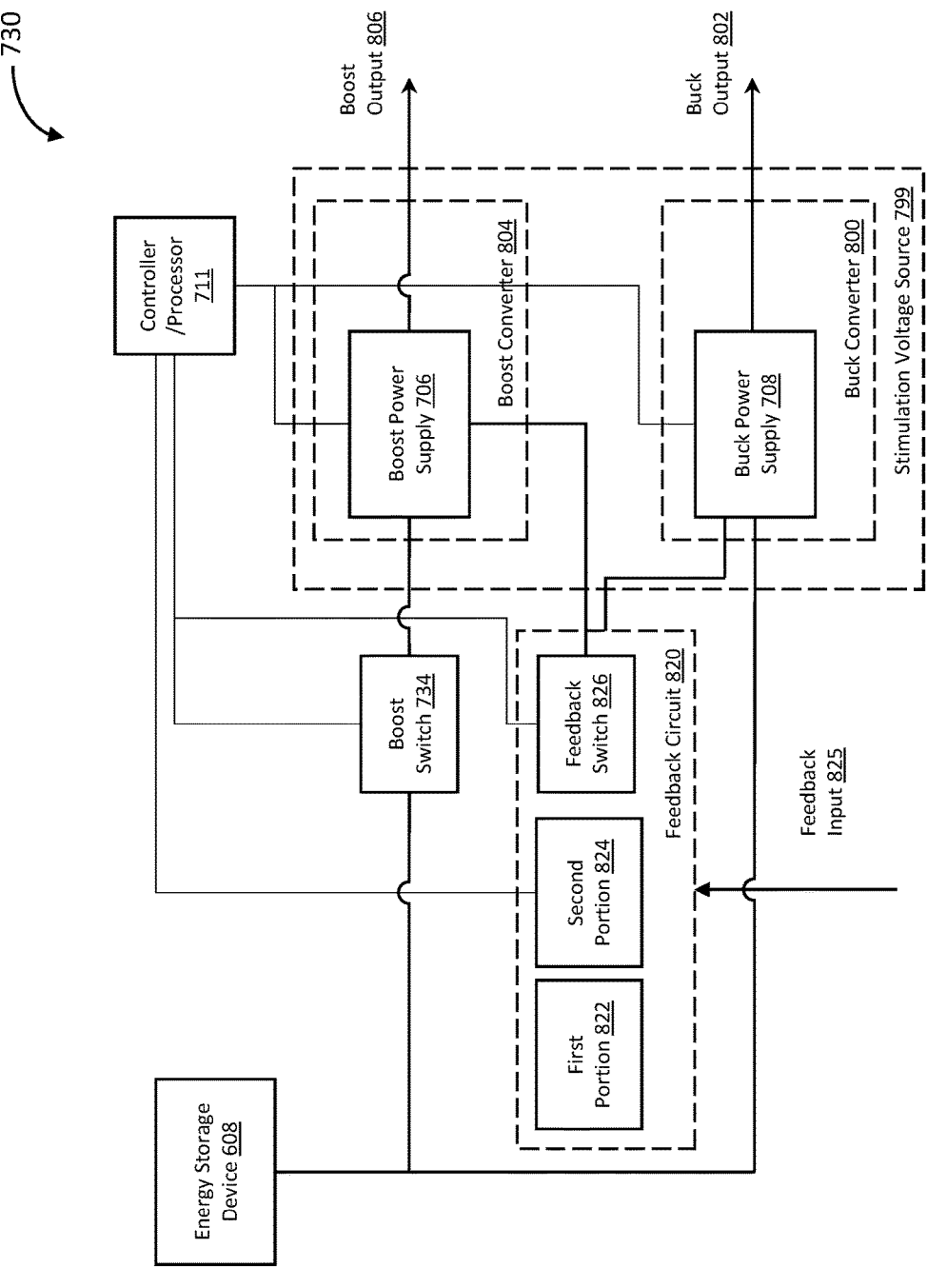
FIG. 4 shows a schematic illustration of one embodiment of circuitry in an IPG including the stimulation circuitry and a feedback signal circuit.

FIG. 4 shows a schematic illustration of one embodiment of circuitry in the IPG 10 including the converter circuitry 730 and a feedback signal circuit 820. The converter circuitry 730 may be controllable by the processor 711 to generate one or several stimulation pulses. The converter circuitry 730 comprises a stimulation voltage source 799 which generates a stimulation voltage to drive at least portions of the stimulation pulse and/or to drive at least portions of a stimulation current. The stimulation voltage source 799 may be a power supply, and specifically a voltage supply that may generate a voltage greater than the voltage of the energy storage device 608, equal to the voltage of the energy storage device 608, and/or less than the voltage of the energy storage device 608. Thus, in some embodiments, the stimulation voltage source 799 may generate at least a portion of a stimulation pulse.

The stimulation voltage source 799 may comprise a voltage reducing circuit such as, for example, a step-down transformer 800 or a buck converter 800. The converter circuitry 730 comprises a buck converter 800. The buck converter 800 may be configured to switch-down the voltage of the energy storage device 608 when stimulation pulses with a voltage lower than the voltage of the energy storage device 608 are desired. The buck converter 800 may be coupled to the one or several switches in the selecting circuit 732 via buck output 802.

The buck converter 800 may include the buck supply 708. The buck supply 708 may, in some embodiments, be a slow turn-on circuit, and in some embodiments, the buck supply 708 may be continuously powered. The buck supply 708 may receive power from the energy storage device 608 and may power the components of the buck converter 800.

The buck converter 800 may include one or several buck energy storage capacitors 803. In some embodiments, the buck energy storage capacitor 803 may be selectively charged and/or discharged according to operation of the buck converter 800.

The converter circuitry 730, and specifically the stimulation voltage source 799 further comprises a voltage increasing circuit such as, for example, a step-up transformer 804 or the boost converter 804. The boost converter 804 may be configured to switch-up the voltage of the energy storage device 608 when stimulation pulses with a voltage higher than the voltage of the energy storage device 608 are desired. The boost converter 804 may be coupled to one or several switches in the selecting circuit 732 via boost output 806.

The boost converter 804 may include the boost supply 706. The boost supply 706 may, in some embodiments, be a fast turn-on circuit, and in some embodiments, the boost supply 706 may be selectably powered.

The boost converter 804 includes and/or is coupled to the boost switch 734 which selectively connects/disconnects the boost converter 804 from the energy storage device 608 to thereby selectably power the boost supply 706. The boost switch 734 may be controllable by the processor 711 to connect the boost converter 804 to the energy storage device 608 when a stimulation pulse from the boost converter 804 is desired. Although FIG. 8 does not include a switch similar to boost switch 734 switchably connecting the buck converter 800 to the energy storage device 608, some embodiments may include a similar switch that switchably connects the buck converter to the energy storage device 608.

The boost converter 804 may comprise one or several boost energy storage capacitors. In some embodiments, the boost energy storage capacitor may be charged by the boost power supply 706. The boost energy storage capacitor may be switchably connected to ground via a boost capacitor switch. In some embodiments, the boost capacitor switch may switchably connect a low-side of the boost energy storage capacitor to ground. The switch, also referred to herein as the low-side switch, may be controlled by the processor 711 to connect the boost energy storage capacitor to ground when the boost converter 804 is not generating a stimulation pulse. In some embodiments, the switchable connection of the low-side of the boost energy storage capacitor 808 to ground may prevent the depletion of energy from the boost energy storage capacitor when the boost converter 804 is not generating a stimulation pulse. This prevents excessive energy loss in the energy storage capacitor due to leakage back into the boost supply 706.

Each of the buck converter 800 and the boost converter 804 are configured to generate a stimulation voltage to drive a stimulation current. In operation, one of the buck converter 800 and the boost converter 804 is selected to generate this stimulation voltage. This selection may be based on, for example, the stimulation voltage and the voltage of the energy storage device 608.

In some embodiments, the IPG 10 may include a feedback signal circuit 820. The feedback signal circuit 820 may be configured to provide a feedback signal to the stimulation circuit 720, and specifically to the buck converter 800 and to the boost converter 804. In some embodiments, the stimulation circuit 720 may modify the stimulation pulse according to the feedback signal. In some embodiments, the feedback signal relates to a voltage of an energy storage capacitor such as the buck energy storage capacitor 803 or the boost energy storage capacitor 808. In some embodiments, the feedback signal relates to a feedback input 825 that is received by the feedback signal circuit 820.

The feedback signal circuit 820 may include a first portion 822 and a second portion 824. The first portion 822 of the feedback signal circuit 820 may be configured to provide a first signal portion, and the second portion 824 of the feedback signal circuit 820 may be configured to provide a second signal portion. In some embodiments, the feedback signal may be based on a combination of the first signal portion and the second signal portion.

The first signal portion may comprise an aspect or parameter of the stimulation pulse, stimulation current or current source. This aspect or parameter of the stimulation pulse may be from a return line of the IPG 10. Specifically, a return line of the IPG 10 may include the current source or current regulator 736. An aspect or parameter of the stimulation pulse and/or the current source 736 may form a portion of the feedback signal. Specifically, an aspect or parameter of phase one of the stimulation pulse passing through the phase one current source 740 may form a portion of the feedback signal. In embodiments in which the phase one current source 740 comprises a set of cascode arranged transistors, the aspect or parameter of the stimulation pulse passing through the phase one current source 740 may comprise a voltage at a node intermediate between the cascode arranged transistors.

The second signal portion may be generated by the second portion 824 of the feedback signal circuit 820, wherein the second portion 824 may comprise a digital-to-analog converter (DAC). In some embodiments, the DAC may be controlled by the processor 711 of the IPG 10 to generate the second signal portion. Specifically, the processor 711 of the IPG 10 may generate a bias current via the DAC based on a voltage sensed from a node in the current source. The processor 711 may, in some embodiments, receive a voltage measurement and/or sense of voltage of a node coupled to the cascode arranged transistors in the return line of the IPG. In some embodiments, this node may be intermediate between the cascode arranged transistors in the return line of the IPG 10 and a ground. Specifically, this node may be coupled to the cascode arranged transistors in the phase one current source 740. In some embodiments, based on this received voltage measurement and/or sensed voltage, the processor 711 may generate a second signal portion, also referred to herein as a bias current or an offset current, via the DAC, to increase a power output of the stimulation circuit 720, to decrease the output of the stimulation circuit 720, or to maintain the output of the stimulation circuit 720.

In one embodiment, the feedback signal may be delivered to the buck converter 800, and may further be selectively delivered to the boost converter 804. Specifically, the feedback signal circuit 820 may include a feedback signal switch 826 which selectively couples the boost converter 804 to the feedback signal circuit 820. In some embodiments, for example, when the boost converter 804 is not generating a stimulation pulse, the feedback signal switch 826 may be controlled by the processor 711 to be open to electrically isolate the boost converter 804 and such that the feedback signal is not delivered to the boost converter 804. In contrast, in the embodiment depicted in FIG. 4, the buck converter 800 is always connected to the feedback signal circuit 820.

Upon receipt of the feedback signal, the one of the buck converter 800 and boost converter 804 generating the stimulation pulse may compare the feedback signal to a predetermined voltage. Specifically, this comparison may be performed by the one of the buck supply 708 and the boost supply 706 generating the stimulation pulse. Based on this comparison, the one of the buck converter 800 and the boost converter 804 may increase, decrease, or maintain its power output, or in other words, may modify the stimulation pulses based on the comparison of the feedback signal to the predetermined value.

Figure 5:
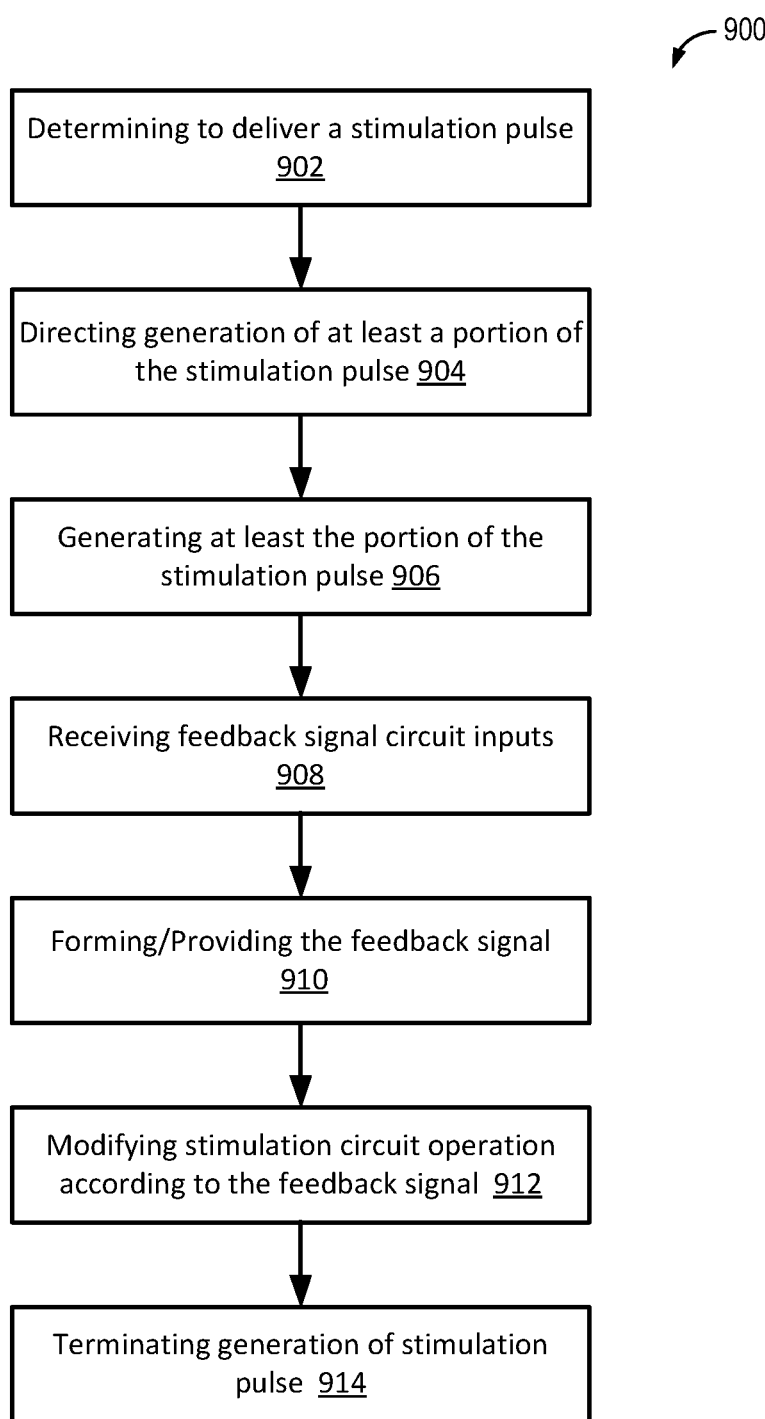
FIG. 5 shows a flowchart illustrating one embodiment of process for generating one or several stimulation pulses.

With reference now to FIG. 5, a flowchart illustrating one embodiment of process for generating one or several stimulation pulses is shown. The process 900 may be performed by an IPG 10. At block 902, the processor 711 determines whether or not to deliver a stimulation pulse. This may include determining to deliver a stimulation pulse with the stimulation circuit 720. In some embodiments, the processor 711 may determine to deliver the stimulation pulse according to one or several programs being executed by the processor 711, which programs may specify one or several attributes of the stimulation pulses including, for example, a frequency of the stimulation pulses, a voltage of the stimulation pulses, a current of the stimulation pulses, a duration of the stimulation pulses, or the like.

At block 904 the processor directs the stimulation circuit 720 to generate the stimulation pulse. In some embodiments, this may include the processor 711 directing the stimulation circuit 720 to generate a portion of the stimulation pulse such as, for example, a first phase of the stimulation pulse. In some embodiments, this may include the processor 711 selecting one of the buck converter 800 and the boost converter 804 for generation of the stimulation pulse and/or for generation of at least a portion of the stimulation pulse.

In some embodiments, directing the stimulation circuit 720 to generate the stimulation pulse may include directing the buck converter 800, and specifically the buck supply 708, to generate the stimulation pulse, and specifically to generate at least the portion of the stimulation pulse.

In some embodiments, directing the generation of the stimulation pulse may include directing the boost converter 804, and specifically the boost supply 706 to generate the stimulation pulse, and controlling switches to connect the boost converter 804. This may include controlling the boost switch 734 to couple the boost power supply 706 to the energy storage device 608, controlling a low-side switch to disconnect the boost energy storage capacitor from ground, and/or the feedback signal switch 826 to connect the feedback signal circuit to the boost converter 800. Thus, in some embodiments, this may include closing the boost switch 734, opening the low-side switch, and closing the feedback signal switch 826.

At block 908, inputs are received by the feedback signal circuit 820. In some embodiments, this may include receiving a voltage at the first portion 822 of the feedback signal circuit 820 and receiving control signals and/or processor outputs at the second portion 824 of the feedback signal circuit 820 or receiving a voltage at the processor 711 from which voltage control signals are generated.

In some embodiments, the input at the first portion 822 may comprise the first signal portion. This input may relate to a voltage on a storage capacitor of the stimulation circuit 720, and specifically on the one of the buck converter 800 and the boost converter 804 that is generating the stimulation pulse. This input may comprise an aspect or parameter of the stimulation pulse, which may be taken from a return line of the IPG 10, and specifically may be taken from the current source 736. In some embodiments, this aspect of the stimulation pulse may be a voltage, and specifically may be a voltage at a node in the current source 736. In some embodiments, this node may be located intermediately between cascode arranged transistors in the current source 736, and specifically may be located intermediately between cascode arranged transistors in the phase one current source 740.

In some embodiments, the input at the second portion 824 may be generated by the processor 711. The processor 711 may receive an input, and based on this input may generate control signals to generate a desired second signal portion. This input may comprise a voltage taken from the return line of the IPG 10. This voltage may be different than the voltage forming the first signal portion, and in some embodiments, this voltage may be taken at a node coupled to the cascode arranged transistors in the return line of the IPG 10, and specifically intermediately between the cascode arranged transistors in the return line of the IPG 10 and a ground.

At block 910 the feedback signal is formed and/or is provided. In some embodiments, this may include generating the second signal portion of the feedback signal with the second portion 824, and specifically with the DAC. In some embodiments, the processor 711 may control the DAC to generate the second signal portion based on voltage inputs received by the processor 711. This may include the processor 711 controlling the DAC to generate a second signal portion to increase a power output of the stimulation circuit 720 above that directed by the first signal portion or to decrease the power output of the stimulation circuit 720 below the power output directed by the first signal portion. Thus, the second signal portion may increase, decrease, or maintain a power output of the stimulation circuit 720.

This second signal portion may be generated by the second portion 824 according to one or several control signals and/or processor outputs. The second signal portion may be added to the first signal portion to form the feedback signal. The feedback signal may then be provided by the feedback signal circuit 820 to the stimulation circuit 720.

At block 912, the stimulation circuit 720 performs the task of modifying its operation according to the feedback signal. In some embodiments, this may include modifying the portion of the stimulation pulse generated by the stimulation circuit 720 according to the feedback signal. This may include increasing the power output of the stimulation circuit 720, or decreasing the power output of the stimulation circuit 720. In some embodiments, the one of the buck converter 800 and boost converter 804 generating the stimulation pulse and receiving the feedback signal may compare the feedback signal to a predetermined voltage. Specifically, this comparison may be performed by the one of the buck supply 708 and the boost supply 706 generating the stimulation pulse. Based on this comparison, the one of the buck converter 800 and the boost converter 804 may increase, decrease, or maintain its power output, or in other words, may modify its operation and/or the stimulation pulses based on the comparison of the feedback signal to the predetermined value.

At block 913, the processor 711 determines whether or not to terminate the stimulation pulse. If the decision is made to not terminate the stimulation pulse, then the process 900 may return to block 904 to further generate and modify the stimulation pulse.

At block 914 the generation of the stimulation pulse is terminated. In some embodiments, this may occur upon completion of generation of stimulation pulse and/or at least the portion of the stimulation pulse. The termination of the generation may include the processor 711 determining to terminate generation of the stimulation pulse and directing the stimulation circuit 720 to terminate generating the stimulation pulse. In some embodiments, directing the stimulation circuit 720 to terminate generation of the stimulation pulse may include directing the buck converter 800, and specifically the buck supply 708, to terminate generation of the stimulation pulse.

In some embodiments, directing the termination of the stimulation pulse may include directing the boost converter 804, and specifically the boost supply 706 to terminate generation of the stimulation pulse, and/or controlling switches to disconnect the boost converter 804. This may include controlling the boost switch 734 to disconnect the boost power supply 706 from the energy storage device 608, controlling the low-side switch 810 to connect the boost energy storage capacitor 808 to ground, and/or the feedback signal switch 826 to disconnect the feedback signal circuit 820 from the boost converter 800. Thus, in some embodiments, and upon completion of generation of at least the portion of the stimulation pulse, this may include opening the boost switch 734, closing the low-side switch 810, and opening the feedback signal switch 826.

Figure 6:
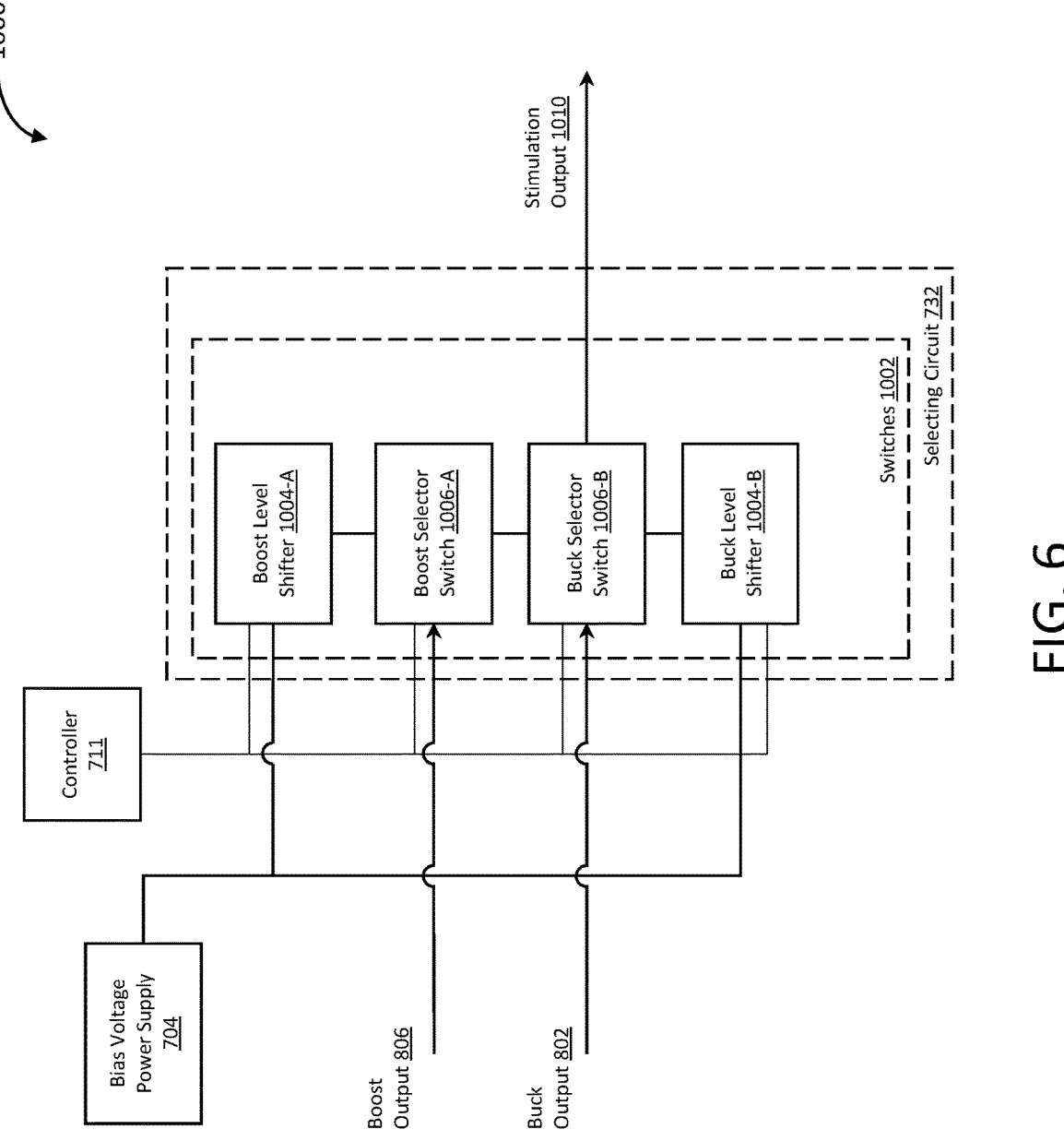
FIG. 6 shows a schematic illustration of one embodiment of switching circuitry including a power supply and the switching matrix.

With reference now to FIG. 6, a schematic illustration of one embodiment of a switching circuit 1000 including the bias voltage power supply 704 and the selecting circuit 732 is shown. Specifically, FIG. 6 depicts the bias voltage power supply 704 and the selecting circuit 732.

In one embodiment, the selecting circuit 732 includes a plurality of switches 1002. In some embodiments, these switches 1002 may comprise analog switches. The switches 1002 include one or more level shifters 1004, and specifically includes two level shifters 1004-A, 1004-B, and one or more stimulation switches 1006, and specifically includes two stimulation switches 1006-A, 1006-B. The level shifters 1004 may bridge from a voltage domain of the processor 711 to a voltage domain of the converter circuitry 730.

The embodiment of FIG. 6 includes level shifters 1004 in pairwise relationships with the stimulation switches 1006. Specifically, each of the level shifters 1004 is coupled to one of the stimulation switches 1006. Thus, a first level shifter 1004-A is coupled to a first stimulation switch 1006-A, and a second level shifter 1004-B is coupled to a second stimulation switch 1006-B. Each of the level shifters 1004-A, 1004-B is configured to maintain a voltage applied to its pairwise coupled one of the stimulation switches 1006-A, 1006-B, at one of the ground voltage, which may be zero volts, or at a voltage output of the bias voltage power supply 704, which may comprise a charge pump. In some embodiments, the charge pump may comprise a plurality of diodes and capacitors. The diode/capacitor voltage multiplier which generates sufficient voltage to power all analog switches 1004, 1006 in the device so proper switch operation can be assured during stimulation pulse delivery. The voltage multiplier is designed to generate either a minimum of 5V, or more than the boost regulator output, whichever is greater.

Each of the stimulation switches 1006-A, 1006-B is coupled to the stimulation circuit 720. Specifically, the first stimulation switch 1006-A is coupled to the boost converter 804 via boost output 806, and the second stimulation switch 1006-B is coupled to the buck converter 800 via buck output 804.

Figure 10:
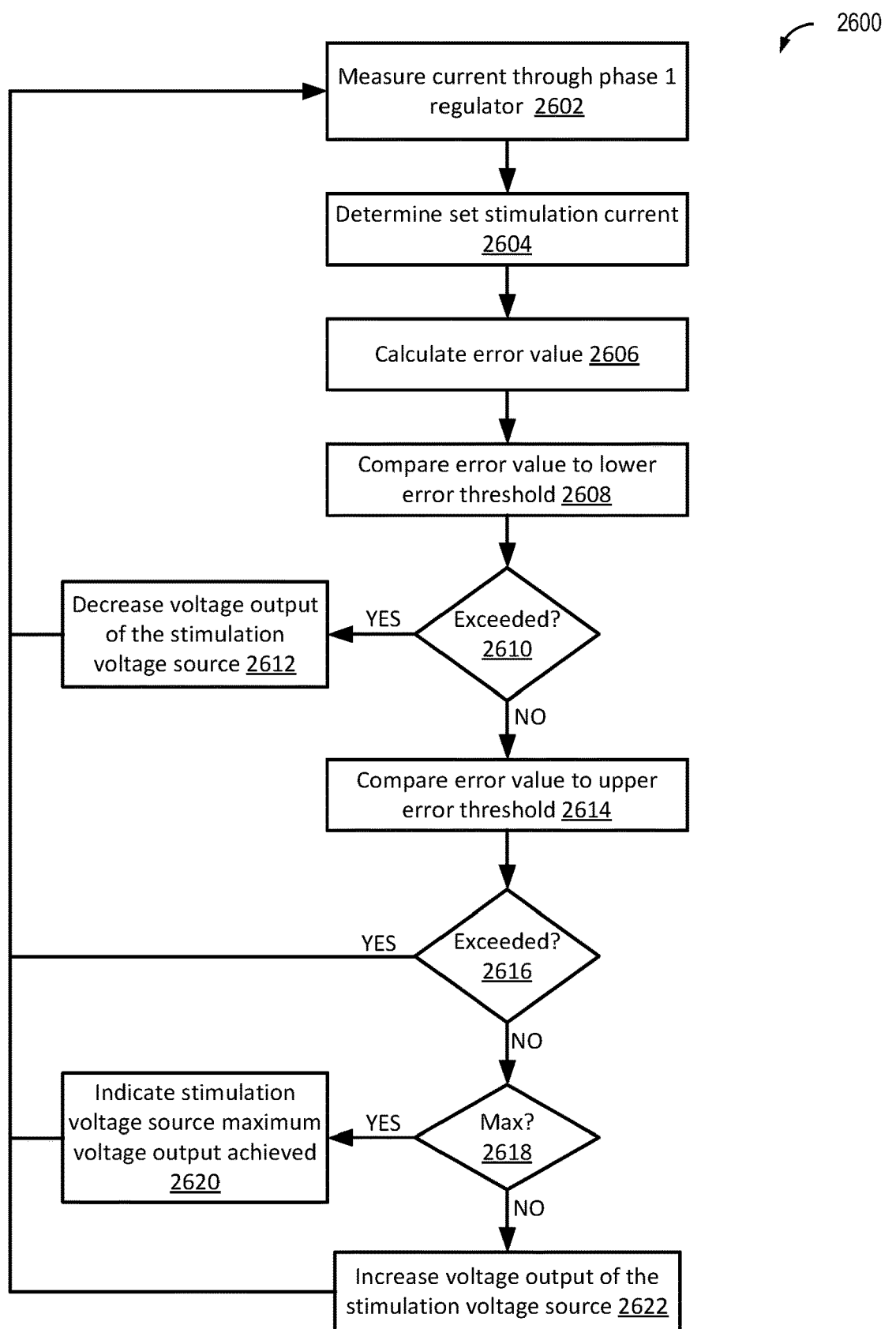
FIG. 10 shows a flowchart illustrating one embodiment of a process for modifying the operation of the stimulation voltage source.

As further seen in FIG. 10, the second stimulation switch 1006-B is directly coupled to the stimulation output 1010, which leads to the switching matrix 724 and to the delivery circuit and/or electrodes 722. The stimulation output 1010 may, in some embodiments, be a stimulation voltage source. In the embodiment of FIG. 10, the first stimulation switch 1006-A, in contrast, is not directly coupled to the stimulation output 1010, but rather is connected to the stimulation output 1010 indirectly via the coupling to the second stimulation switch 1006-B. Thus, the boost converter 804 may be coupled to the delivery circuit and/or one or more electrodes 722 via both the first stimulation switch 1006-A and the second stimulation switch 1006-B. In some embodiments, the processor 711 may control the switches 1002 to couple the desired one of the buck converter 800 and the boost converter 804 to the delivery circuit and/or to one or more electrodes 722.

A process for delivering a stimulation pulse via controlling of the selecting circuit 732 may be described as follows. The process may begin when a bias voltage is generated by the charge pump in the bias voltage power supply 704. This bias voltage is then applied to the selecting circuit 732, and specifically to the switches 1002 in the selecting circuit 732, wherein the switches 1002 may comprise a plurality of analog switches.

As discussed above, in some embodiments, the selecting circuit 732 may comprise at least one level shifter 1004 and at least one stimulation switch 1006. In some embodiments, the selecting circuit 732 may comprise two level shifters 1004-A, 1004-B and two stimulation switches 1006-A, 1006-B, with each of the level shifters 1004 paired with one of the stimulation switches 1006. The level shifters 1004 may maintain a voltage applied to their associated stimulation switch 1006, and specifically at the logic input of their associated stimulation switch 1106 at either a ground voltage, which may be zero volts, or at the voltage output by the charge pump.

Next, a stimulation pulse is generated with the converter circuitry 730. In some embodiments, this may be according to some or all of the steps of process 900 of FIG. 5. The selecting circuit 732 is controlled to couple the converter circuitry 730 to at least one electrode 722. This may include controlling at least one level shifter 1004 to apply a voltage output of the charge pump to the associated stimulation switch 1006 of that level shifter 1004, and controlling that stimulation switch 1006 to couple the stimulation circuitry 720 with at least one electrode 722.

The delivery of the stimulation pulse is completed, and the selecting circuit 732 is controlled to disconnect the stimulation circuitry 720 from the at least one electrode 722. In some embodiments, this may include returning the stimulation switch 1006 to an open position or to a position in which the converter circuitry 730 is not connected to the at least one electrode 722, and controlling the level shifter 1004 such that the ground voltage is applied to the stimulation switch 1006.

The process for controlling the selecting circuit 732 to couple the stimulation circuitry to at least one electrode 722 may be described as follows. First, the one or more level shifters 1004 associated with the one or more stimulation switches 1006 along the path for connecting the converter circuitry 730 with the at least one electrode 722 are switched and/or controlled to apply the voltage output of the charge pump to the one or more stimulation switches 1006 associated with the level shifter(s). In some embodiments, this may include applying the voltage output of the charge pump to the logic control input of each of the one or more stimulation switches 1006 associated with the one or more level shifters 1004.

Next, the one or more stimulation switches 1006 associated with the one or more level shifters 1004 are switched to couple the stimulation circuitry 720 with the at least one electrode 722. In some embodiments, such as is the case with the buck converter 800 of FIG. 4, this may include switching of a single stimulation switch 1006, and in some embodiments, such as is the case of the boost converter 804 of FIG. 4, this may include switching multiple stimulation switches 1006.

The process for controlling the switching matrix 724 to couple the stimulation circuitry 720 to at least one electrode 722 may include the following steps. A first level shifter 1004-A may be switched and/or controlled to apply the voltage output of the bias voltage power supply (e.g., charge pump) to a first stimulation switch 1006-A. In some embodiments, this may include applying the voltage output of the charge pump to the logic control input of the first stimulation switch 1006-A associated with the first level shifter 1004-A. The first stimulation switch 1006-A is switched to couple the stimulation circuitry 720, and specifically the boost converter 804 with the second stimulation switch 1006-B. A second level shifter 1004-B is switched and/or controlled to apply the voltage output of the charge pump to a second stimulation switch 1006-B. In some embodiments, this may include applying the voltage output of the charge pump to the logic control input of the second stimulation switch 1006-B associated with the second level shifter 1004-B.

The second stimulation switch 1006-B is switched to couple the first stimulation switch 1006-A with the at least one electrode 722. In some embodiments, this connecting of the first stimulation switch 1006-A to the at least one electrode 722 via the second stimulation switch 1006-B may connect the boost converter 804 to the at least one electrode 722 via both of the first stimulation switch 1006-A and the second stimulation switch 1006-B.

Figure 7A:
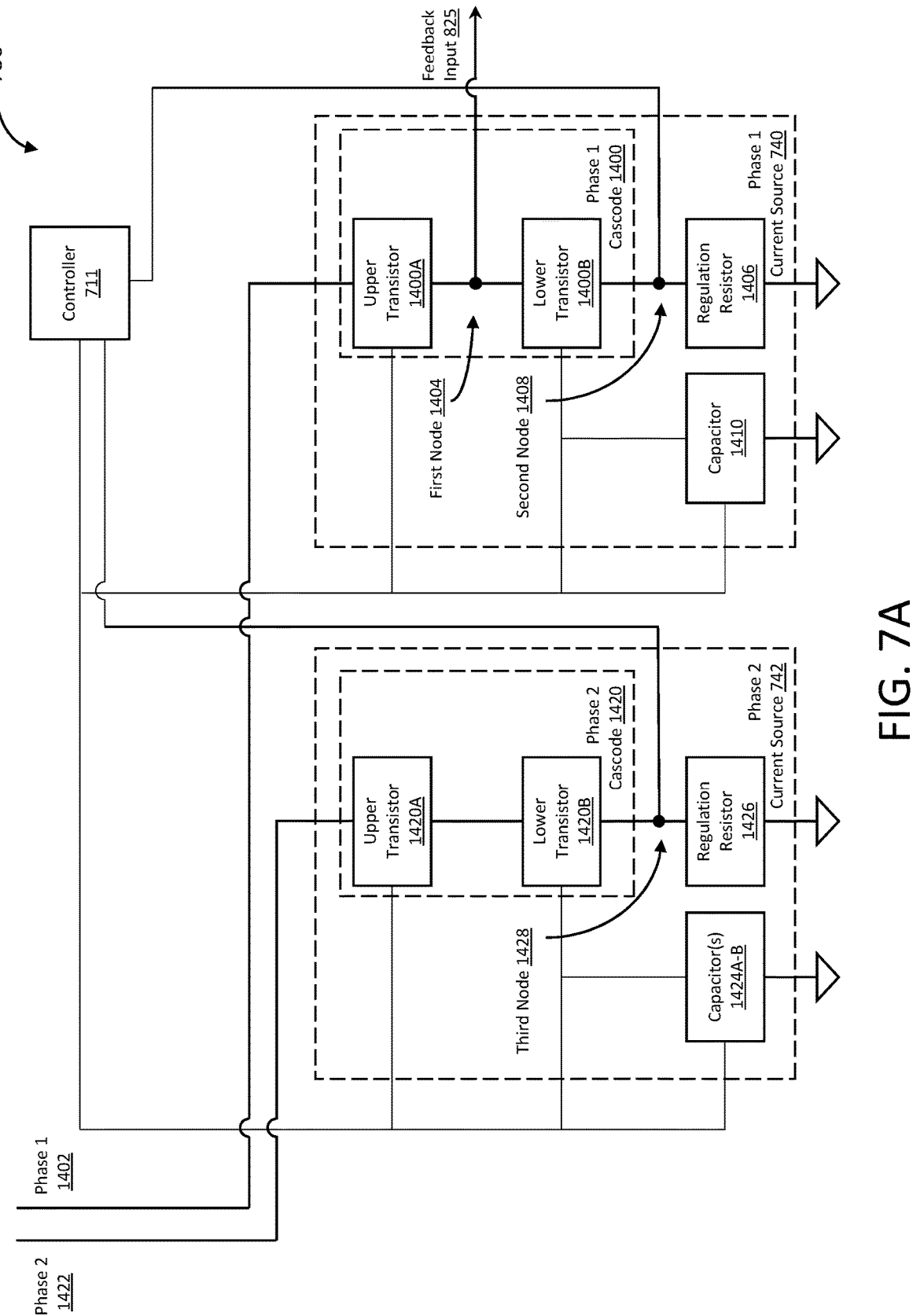
FIG. 7A shows a high-level schematic illustration of one embodiment of a current regulator or current source.

With reference now to FIG. 7A, a high-level schematic illustration of one embodiment of the current source 736 is shown. The current source 736 may include the phase one current source 740 and the phase two current source 742. The phase one current source 740 includes a pair of cascode arranged transistors 1400 that are in, and/or are a part of a return line, and specifically a phase one return line 1402. During a first phase of a stimulation pulse, the stimulation current may pass through the phase one return line 1402 and through the phase one current source 740. Specifically, this current passes through the first set of cascode arranged transistors 1400.

In some embodiments, these cascode arranged transistors 1400 include a first transistor 1400A and a second transistor 1400B. Each of the transistors 1400A, 1400B has a control input to which a voltage may be applied. In some embodiments, the phase one current source 740 may be described as a voltage-driven current source. The voltage applied to these control inputs determines the amount of current allowed through the phase one current source 740, and thus controls and/or limits the current of the first phase of the stimulation pulse. Specifically, the voltage applied to the control input of the first transistor 1400A may either apply no voltage to the first transistor 1400A such that no current passes through the phase one current source 740, or may drive the first transistor 1400A to saturation. Thus, the voltage applied to the control input of the first transistor 1400A may either allow current to pass through the phase one current source 740 or prevent current from passing through the phase one current source 740. In contrast to this, the voltage applied to the control input of the second transistor 1400B may control the amount of current passing through the phase one current source 740. Thus, the first transistor 1400A turns the phase one current source 740 on or off, and the second transistor 1400B throttles current through the phase one current source 740.

The upper or first transistor 1400A may be controlled to limit the range of voltage for which the lower or second transistor 1400B must be controlled to optionally provide a substantially constant stimulation pulse or current.

In some embodiments, the voltage applied to one or both of the control inputs of the transistors 1400A, 1400B may be controlled to achieve a desired current of the first phase of the stimulation pulse. In the embodiment of FIG. 7A, a first regulation voltage, also referred to herein as a first holding voltage, is applied to the control input of one or both of transistor 1400A, 1400B forming the first set of cascode arranged transistors 1400. In some embodiments, this voltage may be applied to the control input of second transistor 1400B by a first voltage holding capacitor 1410. This first voltage holding capacitor 1410 may be charged to a desired voltage, wherein the desired voltage may be a voltage set to achieve a desired current of the first phase of the stimulation pulse. Once the first voltage holding capacitor 1410 has been charged, the first voltage holding capacitor 1410 may apply its voltage to the control input of second transistor 1400B to thereby allow the desired amount of current to flow through the phase one current source 740 during the first phase of a stimulation pulse.

Intermediate between the cascode arranged transistors is a first node 1404. In some embodiments, a voltage measured from this first node 1404 during the first phase of stimulation may comprise the first signal portion forming part of the feedback signal provided by the feedback signal circuit 820 to the stimulation circuit 720. This measured voltage may be transmitted via the feedback input 825. Thus, in some embodiments, a voltage of the first node 1404 and/or taken from the first node 1404 affects operation of the stimulation circuit 720 during the first phase of the stimulation and/or of the stimulation pulse. The first node 1404 between the two transistors 1400A/1400B is connected to the first signal portion feedback signal circuit 822 to assure there is just sufficient voltage on the stimulation output to keep the lower transistor 1400B with a very small voltage across it. This minimizes power loss that would be caused by having excessive voltage across the cascode, yet assures the cascode stays in the current regulating region. The voltage margin on the phase one cascode is fine-tuned by software in the processor 711 by varying offset current into the return signal feedback path using a digitally operated resistor array DAC of the second feedback circuit portion 824.

The phase one current source 740 further includes a regulation resistor 1406. The regulation resistor 1406 is coupled to the first set of cascode arranged transistors 1400, and specifically is located between these cascode arranged transistors 1400 and the ground. Intermediate between the first set of cascode arranged transistors 1400 and the regulation resistor 1406 is a second node 1408. In some embodiments, the processor 711 is configured to sense, measure, and/or receive the voltage from the second node 1408 and use this voltage of the second node 1408 in controlling the DAC to generate the second signal portion forming part of the feedback signal provided by the feedback signal circuit 820 to the stimulation circuit 720. Thus, in some embodiments, a voltage of the second node 1408 and/or taken from the second node 1408 affects operation of the stimulation circuit 720 during the first phase of the stimulation and/or of the stimulation pulse. More specifically, in some embodiments, the processor 711 affects operation of the stimulation circuit 720 via control of the DAC based on the voltage of that second node 1408.

The phase two current source 742 includes a pair of cascode arranged transistors 1420 that are in, and/or are a part of a return line, and specifically a phase two return line 1422. During a second phase of a stimulation pulse, the stimulation current may pass through the phase two return line 1422 and through the phase two current source 742. Specifically, this current passes through the second set of cascode arranged transistors 1420.

This second set of cascode arranged transistors 1420 includes a first transistor 1420A and a second transistor 1420B. Each of the transistors 1420A, 1420B has a control input to which a voltage may be applied. In one embodiment, the phase two current source 742 may be described as a voltage-driven current source. The voltage applied to these control inputs determines the amount of current allowed through the phase two current source 742, and thus controls and/or limits the current of the second phase of the stimulation pulse.

In some embodiments, a first phase of the stimulation pulse is generated by the stimulation circuit 720. This first phase of the stimulation pulse may charge one or several coupling or series capacitors. When the first phase of the stimulation pulse has terminated and thus the stimulation circuit 720 is no longer driving the stimulation pulse, the second phase begins in which those one or several charged coupling capacitors discharges. The energy stored in the capacitor during the first phase of the stimulation current is used to generate the stimulation current during the second phase thereby reducing the energy withdrawn from the energy source. The rate of the discharge of the capacitor(s) and, thus, the duration of the second phase is controlled by the phase two current source 742.

In some embodiments, the voltage applied to one or both of the control inputs of the second set of transistors 1420 may be controlled to achieve a desired current of the second phase of the stimulation pulse. In at least one embodiment of FIG. 7A, a second regulation voltage, also referred to herein as a second holding voltage, is applied to the control input of one or both of the transistors 1420A, 1420B forming the second set of cascode arranged transistors 1420. In some embodiments, this voltage may be applied to the control input of the second transistor 1420B by one or several second voltage holding capacitors 1424-A, 1424-B. These one or several second voltage holding capacitors 1424-A, 1424-B may be charged to a desired voltage, wherein the desired voltage may be a voltage selected to achieve a desired current of the second phase of the stimulation pulse. Once the one or several second voltage holding capacitors 1424-A, 1424-B have been charged, the one or several second voltage holding capacitors 1424-A, 1424-B may apply their voltage to the control input of the second transistor 1420B to allow the desired amount of current to flow through the phase two current source 742 during the second phase of a stimulation pulse.

The phase two current source 742 further includes a second regulation resistor 1426. The second regulation resistor 1426 is coupled to the second set of cascode arranged transistors 1420, and specifically is located between these cascode arranged transistors 1420 and the ground. Intermediate between the second set of cascode arranged transistors 1420 and the regulation resistor 1426 is a third node 1428.

As seen in FIG. 14, the IPG 10 includes a current regulation digital-to-analog converter (DAC) 1430. The current regulation DAC 1430 selectively delivers and/or applies a voltage to the control inputs of one or more of the transistors in the set of cascode arranged transistors 1400, 1420 of the phase one current source 740 and/or the phase two current source 742. Specifically, the current regulation DAC 1430 may apply a voltage to the control inputs of one or more of the transistors in the set of cascode arranged transistors 1400, 1420 of the phase one current source 740 and/or the phase two current source 742 via charging the first voltage holding capacitor 1410 and/or the one or several second voltage holding capacitors 1424-A, 1424-B. In some embodiments, the current regulation DAC 1430 may be controlled by the processor 711 to apply one or several desired and/or predetermined voltages to the control inputs of one or more of the transistors in the set of cascode arranged transistors 1400, 1420 of the phase one current source 740 and/or the phase two current source 742.

The constant voltage on the lower control input of each current source 740, 742 (the control inputs of the transistors 1420B, 1400B forming the second set of cascode arranged transistors 1420) circuit is held constant with capacitors 1410, 1424-A, 1424-B on each control input. Software in the processor 711 monitors the cascode current by monitoring the voltage of the regulation resistors 1406, 1426, and as needed connects the corresponding capacitors 1410, 1424-A, 1424-B to the DAC 1430 to fine tune the capacitor voltage to achieve the target stimulation current. To minimize the holding capacitor voltage drop and because transistor control inputs can have current leakage, extremely low leakage analog switches U504A, U504D connect the hold capacitors 1410, 1424-A, 1424-B to the MOSFET gates during stimulation pulse delivery.

Figure 7B:
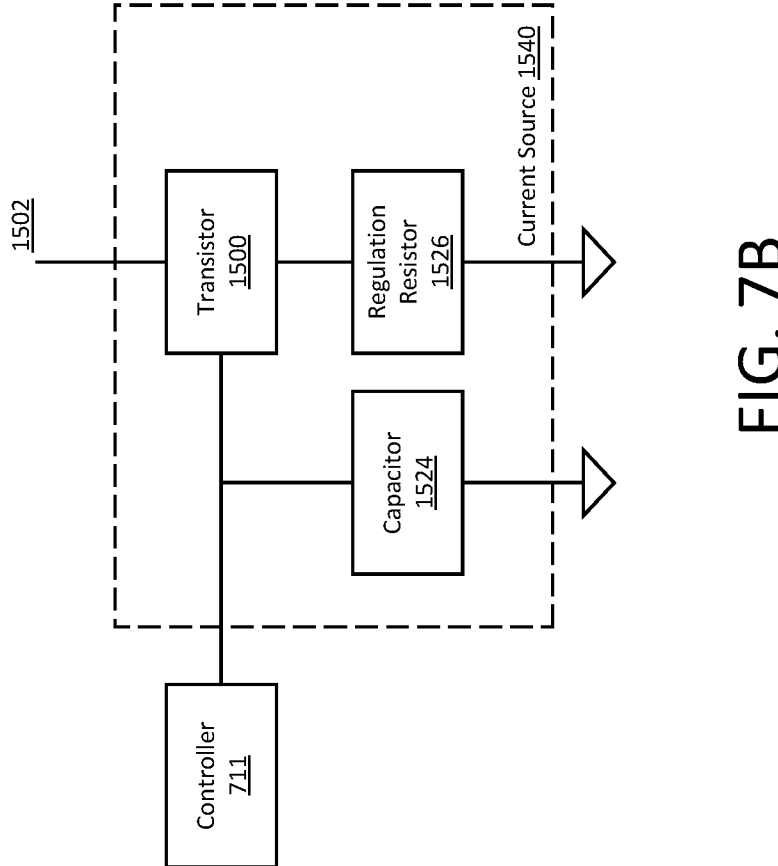
FIG. 7B shows a high-level schematic illustration of a first alternative embodiment of a current regulator or current source.
Figure 7C:
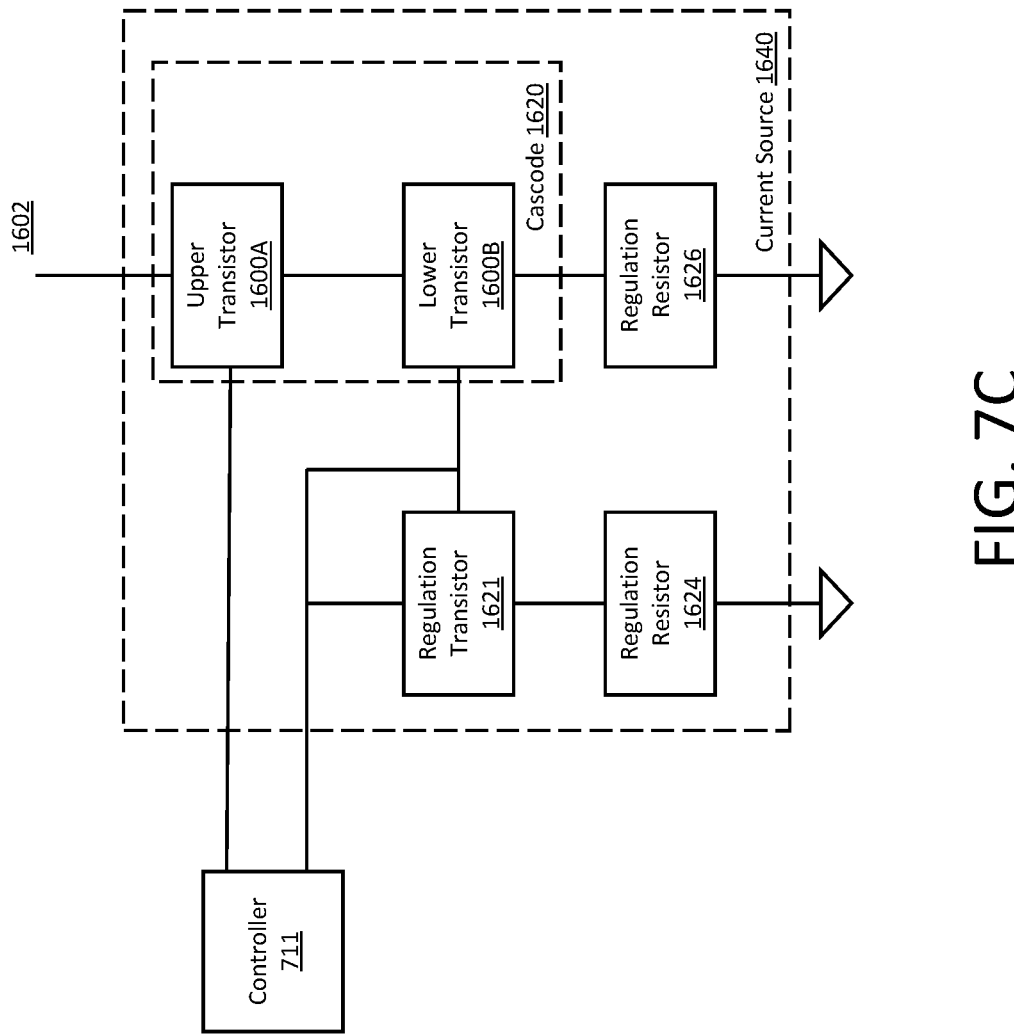
FIG. 7C shows a high-level schematic illustration of a second alternative embodiment of a current regulator or current source.

As shown in FIGS. 7B and 7C, the current regulator may include alternative embodiments. In a first alternative embodiment, shown in FIG. 7B, a single transistor 1500 (e.g. a MOSFET) may be employed in the first current source 1540. The single MOSFET 1500 is controlled by the controller 711 to control the current provided through the phase output line 1502 during the first phase. The controller 711 may operate through a digital to analog converter (DAC) which is operatively connected to the gate of the transistor 1500. The upper MOSFET 1400A included in the embodiment shown in FIG. 7A is eliminated in the embodiment shown in FIG. 7B. The current source 1540 may include a capacitor 1524 and regulation resistor 1526 that function in the same manner described above with regard to the embodiment shown in FIG. 7A. Although described as a phase one current source, the current source shown in FIG. 7B could be employed as a phase two current source.

In a second alternative embodiment, shown in FIG. 14C, the phase one current source includes a current mirror. However, the typical current mirror structure is modified to include an upper transistor (e.g., a MOSFET). The upper transistor 1600A is controlled to limit the range of voltage over which the lower transistor 1600B (which is part of the current mirror) must operate. The upper and lower transistors 1600A, 1600B form a cascode structure. The transistors are controlled to provide a substantially constant stimulation current or pulse. The controller 711 controls the current mirror which includes a regulation transistor 1621, a regulation resistor 1624, the lower transistor 1600B and the regulation resistor 1626. The controller 711 may operate through a digital to analog converter (DAC) which is operatively connected to the gates of the transistors 1600A, 1600B and 1621. The controller 711 may operator to provide a substantially constant current through the phase output line 1602. Although described as a phase one current source, the current source shown in FIG. 7C could be employed as a phase two current source.

FIG. 8 depicts a simplified schematic showing how the current regulator is operatively connected to the voltage supply (i.e., voltage converter or converter circuit 730) and the switching matrix 724. The current sources operate to pull down current from the electrodes 722 through the switching matrix 724. As shown in FIG. 8, and mentioned above, the IPG may include series capacitors that are configured to discharge through the current regulator during the second phase.

The process for generating the stimulation pulse may be generally described as follows. In some embodiments, the stimulation pulse may be generated by or with the converter circuitry 730. The current of the stimulation pulse is controlled via the current source 736. In some embodiments, the current source may include on or several sets of cascode arranged transistors. In some embodiments, the current allowed through the current source 736 may be controlled by application of a voltage to a control input of at least one of the one or several sets of cascode arranged transistors 1400, 1420. In some embodiments, the current source 736 may comprise a phase one current source 740 and a phase two current source 742. In some embodiments, each of the phase one current source 740 and the phase two current source 742 may comprise a set of cascode arranged transistors such that the phase one current source 740 comprises a first set of cascode arranged transistors 1400 and the phase two current source 742 comprises a second set of cascode arranged transistors 1420.

In some embodiments, the phase one current source 740 may control the current of the stimulation pulse during a first phase, and the phase two current source 742 may control the current of the stimulation pulse during a second phase. In some embodiments, the current allowed through the phase one current source 740 may be controlled by application of voltage to a control input of at least one of transistors in the set of cascode arranged transistors 1400 in the phase one current source 740. Likewise, in some embodiments, the current allowed through the phase two current source 742 may be controlled by application of voltage to a control input of at least one of transistors in the set of cascode arranged transistors 1420 in the phase two current source 742.

A voltage downstream of a portion of the current source 736 is received and/or sensed by a processor 711. In some embodiments, this voltage may be from the second node 1408, and this voltage may comprise the second signal portion. The processor 711 may control a power output of the stimulation circuit 730 based on the received and/or sensed voltage. In some embodiments, this may include the processor 711 controlling a DAC to generate a second signal portion that may form all or parts of the feedback signal that may control and/or affect power output of the stimulation circuit 720. The feedback signal may be provided to the stimulation circuit 720, and may affect the operation of the stimulation circuit 720, and specifically may affect the power output of the one of the buck converter 800 and the boost converter 804 generating the stimulation pulse.

A regulation voltage is applied to a control input of one of a set of cascode arranged transistors. In some embodiments, this voltage may control the amount of current allowed to flow through the set of cascode arranged transistors. In some embodiments, the current source may include a voltage holding capacitor which may be connected to the control input of the one of the set of cascode arranged transistors. This voltage holding capacitor may be charged to a regulation voltage, and the charged voltage holding capacitor may apply this regulation voltage to the control input of the one of the set of cascode arranged transistors.

A first current during a first phase of the stimulation pulse is controlled with a phase one current source 740. A second current during a second phase of the stimulation pulse is controlled with a phase two current source 742. In some embodiments, each of the phase one current source 740 and the phase two current source 742 may comprise a set of cascode arranged transistors, and controlling the current may comprise applying a regulation voltage to the control input of at least one transistor in the set of cascode arranged transistors.

A first regulation voltage is applied to a control input of one of a first set of cascode arranged transistors 1400. In some embodiments, this voltage may control the amount of current allowed to flow through the first set of cascode arranged transistors 1400. A second regulation voltage is applied to a control input of one of a second set of cascode arranged transistors 1420. In some embodiments, this voltage may control the amount of current allowed to flow through the second set of cascode arranged transistors 1420.

In some embodiments, each of these sources 740, 742 may further include a voltage holding capacitor. The voltage holding capacitor is coupled to the control input of the transistor in the regulators set of cascode arranged transistors so that a voltage of that voltage holding capacitor is applied to the control input. In such embodiments, this voltage holding capacitor may be charged to a regulation voltage, and the charged voltage holding capacitor may apply this regulation voltage to the control input of the one of the set of cascode arranged transistors. In some embodiments, applying the first regulation voltage to the control input of the at least one of the first set of cascode arranged transistors may include charging the first voltage holding capacitor to the first regulation voltage, and, in some embodiments, applying the first regulation voltage to the control input of the at least one of the first set of cascode arranged transistors may include charging the second voltage holding capacitor to the second regulation voltage.

With reference now to FIG. 9, a flowchart illustrating one embodiment of a process 2500 for high-level control of an IPG 10, and specifically for delivering a stimulation pulse with the IPG 10. The process 2500 may be performed by all or portions of the IPG 10, including by the processor 711, the converter circuitry 730, and/or the current source 736. The process 2500 begins at block 2502, wherein it is determined to generate and deliver one or several stimulation pulses. In some embodiments, this determination may be made based on a received request and/or signal, and in some embodiments, the processor 711 may determine based on information contained in and/or generated by the IPG 10 to generate and deliver one or several stimulation pulses. In some embodiments, for example, the processor 711 may determine to generate and deliver one or several stimulation pulses based on, for example, an amount of elapsed time since delivery of one or several most recent previous stimulation pulses. The processor 711 may determine to generate and deliver the one or several stimulation pulses according to a stimulation program and/or pulse program.

At block 2504, the stimulation voltage and/or current for the one or several stimulation pulses is determined, received, and/or retrieved. In some embodiments, this may comprise receiving, determining, and/or retrieving one or several desired parameters of the one or several stimulation pulses. These one or several desired parameters may include, for example, a desired voltage of a stimulation voltage and/or a desired current of a stimulation current. In some embodiments, for example, the desired voltage and/or current of the stimulation pulse is determined, received, and/or retrieved by the processor 711 based on, for example, the stimulation program and/or the pulse program. In some embodiments, the desired stimulation voltage and/or current may also be determined, received, and/or retrieved based on information received from the patient such as, for example, information received from the clinician programmer 60 and/or from the patient remote 70.

At block 2506, one of a voltage reducing circuit and a voltage increasing circuit is selected for generation of the stimulation voltage. In some embodiments, the voltage reducing circuit may comprise the buck converter 800 and in some embodiments, the voltage increasing circuit may comprise the boost converter 804. In some embodiment, the stimulation voltage may be the voltage generated by the selected one of the buck converter 800 and the boost converter 804, wherein the voltage drives the stimulation current. In some embodiments, the one of the buck converter 800 and the boost converter 804 may be selected based on one or several attributes of the one or several stimulation pulses and/or one or several attributes of the IPG 10. In some embodiments, for example, the one of the buck converter 800 and the boost converter 804 may be selected based on the desired stimulation voltage and/or stimulation current and/or the voltage of the energy storage device 608. The one of the buck converter 800 and the boost converter 804 may be selected by the processor 711.

At block 2508, the current source is set for generation of a stimulation current, or in other words set to generate the stimulation current having the value of the desired current of block 2504. In some embodiments, this may include, for example, the calibration of the current source, testing the current sources, and/or generating and applying a compensation formula. In some embodiments, setting the current source may include, for example, setting the holding voltage of the phase one current source 740 and/or of the phase two current source 742 to a desired voltage for generation of a desired stimulation current.

At block 2510, the selected one of the voltage decreasing circuit such as the buck converter 800 and the voltage increasing circuit such as the boost converter 804 may be controlled to generate the desired stimulation voltage. In some embodiments, this may include, for example, enabling the one of the selected buck converter 800 and the boost converter 804 to generate the stimulation voltage, specifically by controlling the power supply of the one of the selected buck converter 800 and the boost converter 804.

At block 2512, one or several stimulation parameters are measured, determined, and/or detected. In some embodiments, these one or several stimulation parameters may be parameters of at least one delivered stimulation pulse. In some embodiments, this may include, for example, the measuring of the stimulation current passing through the current source 736, and in some embodiments, measuring the current passing through the phase one current source 740. In some embodiments the current passing through the phase one current source 740 may be measured and/or determined via measuring at the second node 1408, and specifically via voltage measurement at the second node 1408.

At block 2514, the operation of the stimulation voltage source 799, and specifically of one of the voltage decreasing circuit such as the buck convertor 800 and the voltage increasing circuit such as the boost converter 804 is modified. In some embodiments, the operation of the stimulation voltage source 799, and specifically of the selected one of the voltage decreasing circuit such as the buck convertor 800 and the voltage increasing circuit such as the boost converter 804 may be modified based on one or several parameters of a delivered stimulation pulse.

In some embodiments, this may include affecting operation of the selected one of the buck converter 800 and the boost converter 804 to increase or decrease the stimulation voltage, or to switch from selection of one of the buck converter 800 and boost converter 804 for generation of the stimulation voltage to the other of the buck converter 800 and the boost converter 804. In some embodiments the modification of the operation of the selected one of the buck converter 800 and the boost converter 804 may be conducted using the feedback signal from the feedback signal circuit 820.

With reference now to FIG. 10, a flowchart illustrating one embodiment of a process 2600 for modifying the operation of the stimulation voltage source 799, and specifically of one of the buck convertor 800 and the boost converter 804 is shown. The process 2600 may be performed as a part of, or in the place of the step of block 2514 of FIG. 25.

The process 2600 begins at block 2602, wherein current through the current source 736, and specifically through the phase one current source 740 is measured. In some embodiments the current passing through the phase one current source 740 may be measured and/or determined via measurement at the second node 1408, and specifically via voltage measurement at the second node 1408. The current through the current source 736 may be an actual stimulation current.

At block 2604, a set stimulation current is determined. In some embodiments, this may include determining the current set to pass through the current source 736, and in some embodiments, set to pass through the phase one current source 740. In some embodiments, this current may be set at block 2508 of process 2500.

At block 2606, an error value may be calculated. In some embodiments, the error value may characterize the difference between the set current and the actual current measured through the current source 736, and specifically through the phase one current source 740. In some embodiments, the error value may characterize an amount that the actual current measured through the current source 736 is less than the set stimulation current. The error value may be calculated by the processor 711.

At block 2608, the error value is compared to a first error threshold, which may be a lower error threshold. In some embodiments, the first error threshold may identify circumstances in which the actual current measured through the current source 736 is too close to the set current, and thus when the magnitude of the error value is too small. In some embodiments, for example, efficiency of the IPG 10 may be lost if the actual stimulation current measured through the current source 736 is too close to the set stimulation current. This may occur because the selected one of the buck converter 800 or boost converter 804 may be outputting a voltage in excess of the voltage needed to provide a desired stimulation voltage. To prevent this circumstance from arising, and to improve efficiency, the first error threshold may be used to identify circumstances in which the measured stimulation current is too high, and may thereby allow control of the buck converter 800 and the boost converter 804 to improve efficiency. This comparison may be performed by the processor 711.

At decision step 2610, it is determined if the first error threshold is exceeded, or in other words, if the actual stimulation current measured through the current source 736 is too close to the set stimulation current. If it is determined that the first error threshold is exceeded, then the process 2600 proceeds to block 2612, and the stimulation voltage source 799 is controlled to decrease its voltage output. In other words, the selected one of the buck converter 800 and the boost converter 804 is controlled to decrease its voltage output. In some embodiments, this may include decreasing the headroom of the stimulation voltage source 799 and specifically of the selected one of the voltage increasing circuit and the voltage decreasing circuit. After the stimulation voltage source 799 has been controlled to decrease its voltage output, the process 2600 returns to block 2602 and proceeds as outlined above.

Returning again to decision step 2610, if it is determined that the first error threshold is not exceeded, then the process 2600 proceeds to block 2614, wherein the error value is compared to a second error threshold, which may be an upper threshold error. In some embodiments, the second error threshold may identify circumstances in which the actual current measured through the current source 736 is too different from the set current, and thus when the magnitude of the error value is too large. If the magnitude of the error value is too large, then the stimulation current may be inadequate to achieve a desired effect. To prevent this circumstance from arising, the second error threshold may be used to identify circumstances in which the measured stimulation current is too low, and may thereby allow control of the buck converter 800 and the boost converter 804 to increase the stimulation current. This comparison may be performed by the processor 711.

At decision step 2616, it is determined if the second error threshold is exceeded, or in other words, if the actual stimulation current measured through the current source 736 is too low as compared to the set stimulation current. If it is determined that the second error threshold is exceeded, and thus the actual stimulation current is not too low, then the process 2600 returns to block 2602 and proceeds as outlined above.

Returning again to decision step 2616, if it is determined that the second error threshold is not exceeded, or in other words, it is determined that the stimulation current is too low, then the process 2600 proceeds to decision step 2618, wherein it is determined if the stimulation voltage source 799 is outputting a maximum stimulation voltage. In some embodiments, this maximum stimulation voltage may be a fixed value, or may vary based on one or several parameters of the IPG 10 such as, for example, a voltage of the energy storage device 608.

If it is determined that the stimulation voltage source 799 is outputting a maximum stimulation voltage, then the process 2600 proceeds to block 2620, wherein it is indicated that the stimulation voltage source 799 maximum voltage output is achieved. In some embodiments, this may include adding a value to a database indicating that the stimulation voltage source 799 is delivering its maximum voltage output. In some embodiments, in which the buck converter 800 is selected to generate the stimulation voltage, a determination that the buck converter 800 is operating at is maximum voltage output may result in switching to use of the boost converter 804 which may generate a larger stimulation voltage. In some embodiments, and after indicating that the stimulation voltage source 799 is outputting a maximum stimulation voltage, the process 2600 proceeds to block 2602 and continues as outlined above.

Returning again to decision state 2618, if it is determined that the stimulation voltage source 799 is not outputting a maximum stimulation voltage, then the process 2600 proceeds to block 2622, wherein the voltage output of the stimulation voltage source 799 is increased. In other words, the selected one of the voltage decreasing circuit such as, for example, the buck converter 800 and the voltage increasing circuit such as, for example, the boost converter 804 is controlled to increase its voltage output. In some embodiments, controlling the selected one of the voltage decreasing circuit and the voltage increasing circuit to increase the voltage output may include, for example, increasing the headroom of the selected one of the voltage decreasing circuit and the voltage increasing circuit. After the stimulation voltage source 799 has been controlled to increase its voltage output, the process 2600 returns to block 2602 and proceeds as outlined above.

Figure 11:
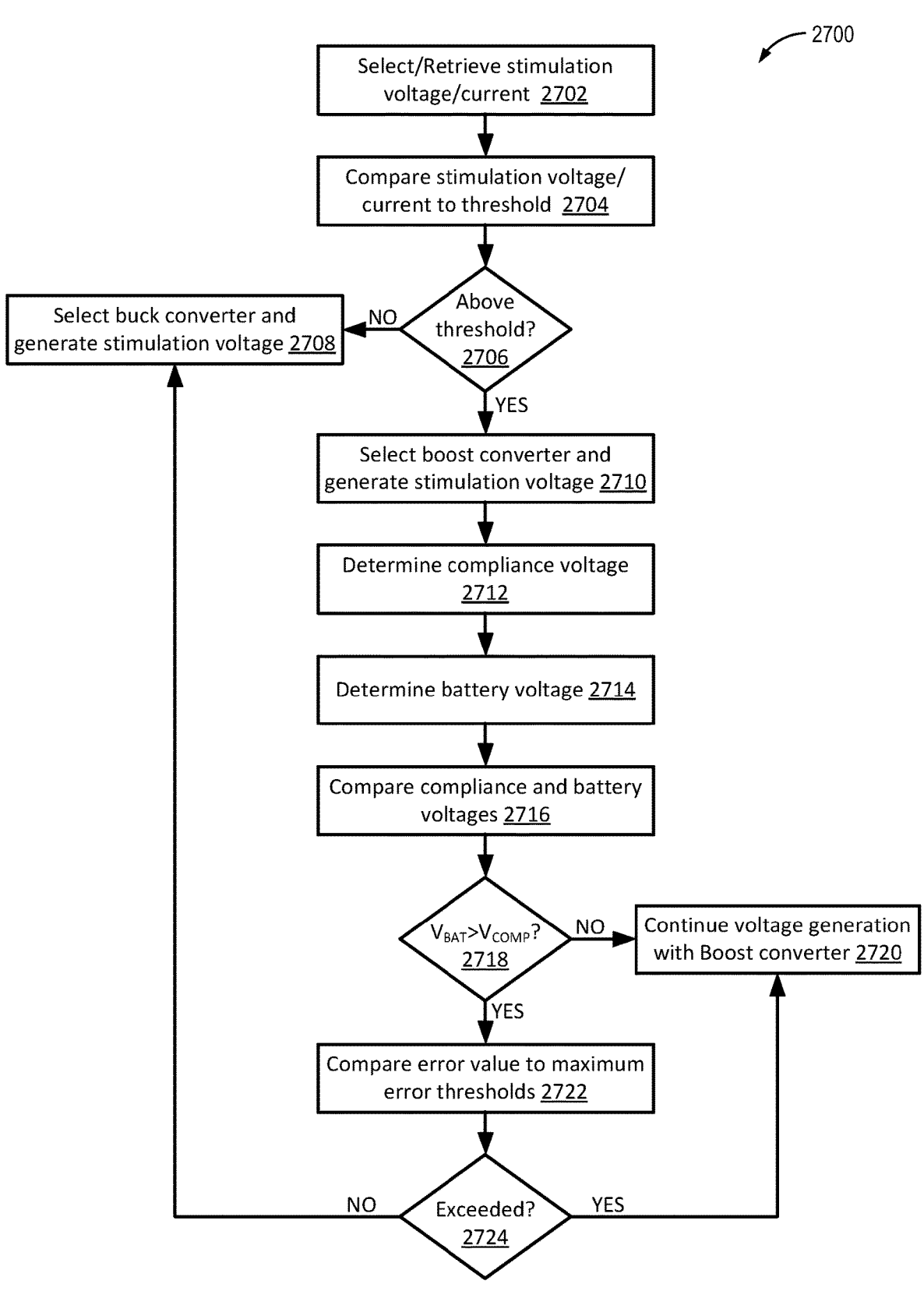
FIG. 11 shows a flowchart illustrating one embodiment of a process for selecting one of a voltage increasing circuit and a voltage decreasing circuit for generation of the stimulation voltage.

With reference to FIG. 11, a flowchart illustrating one embodiment of a process 2700 for selecting one of the buck converter 800 and the boost converter 804 for generation of the stimulation voltage is shown. In some embodiments, the process 2700 may be performed as a part of, or in the place of the step of block 2506 of process 2500. The process 2700 may be performed by all or portions of the IPG 10, including by the processor 711.

The process 2700 begins at block 2702, wherein a desired stimulation voltage and/or current is identified, selected, and/or retrieved. In some embodiments, this may include the identification, selection, and/or retrieving of information identifying a desired stimulation voltage and/or current. In some embodiments, the desired stimulation voltage may be a voltage for the stimulation voltage source 799 to generate to drive stimulation current during at least a portion of the stimulation pulse and the stimulation current may be the desired current of at least a portion of one or several stimulation pulses, and specifically during all or portions of phase one of the stimulation pulse. In some embodiments, the processor 711 may select, identify, and/or retrieve a desired stimulation voltage and/or desired stimulation current from, for example, a stimulation program and/or a pulse program.

At block 2704, the desired stimulation voltage and/or desired stimulation current are compared to a threshold value. In some embodiments, this threshold value may characterize a stimulation voltage threshold, or a stimulation current threshold. In some embodiments, for example, the threshold may identify a current such as approximately 200 μA, approximately 300 μA, approximately 400 μA, approximately 500 μA, approximately 600 μA, approximately 700 μA, approximately 800 μA, between approximately 300 μA and 600 μA, or any other or intermediate current.

At decision step 2706, it is determined if the desired stimulation voltage and/or desired current of block 2702 is greater than the threshold value of block 2704. In some embodiments, this determination may be made based on the comparison of block 2704. In some embodiments, the comparison of block 2704 and/or the determination of block 2706 may be made by the processor 711.

If it is determined that the desired stimulation voltage and/or desired stimulation current of block 2702 is less than the threshold value, then the process 2700 proceeds to block 2708 and selects a voltage decreasing circuit, such as the buck converter 800, and generates the stimulation voltage with the voltage decreasing circuit such as the buck converter 800.

Returning again to decision step 2706, if it is determined that the stimulation voltage and/or stimulation current of block 2702 is greater than the threshold value of block 2704, then the process 2700 proceeds to block 2710, wherein a voltage increasing circuit, such as the boost converter 804 is selected, and the stimulation voltage is generated with the voltage increasing circuit such as the boost converter 804.

At block 2712 a compliance voltage is determined. In some embodiments, the compliance voltage may be the voltage difference between a source electrode and a sink electrode for a stimulation pulse. The compliance voltage may be determined by the processor 711. In some embodiments, determining the compliance voltage may include, for example, determining the difference between the voltage of the electrode serving as the anode and the voltage of the electrode serving as the cathode. The voltage of the anode and the cathode may be determined by a measurement of the stimulation voltage generated by the stimulation voltage source 799 and a voltage of the phase one return line 1402.

In some embodiments, determining the compliance voltage may further include determining an adjusted compliance voltage by adjusting the compliance voltage by adding a headroom voltage to the difference between the voltage of the electrode serving as the anode and the voltage of the electrode serving as the cathode. This headroom may, in some embodiment, account for one or several voltage drops including, for example, a voltage drop across the current source 736, and specifically across the phase one current source 740, and a margin voltage. In some embodiments, the voltage drop across the phase one current source 740 may include, for example, a voltage drop across the first set of cascode arranged transistors 1400 and a voltage drop across the regulation resistor 1406. In some embodiments, the margin voltage may be a fixed margin and may comprise a value between, for example, 10 mV and 100 mV.

At block 2714, a voltage of the energy storage device 608 is determined. At block 2716, the compliance voltage, and/or the adjusted compliance voltage, and the voltage of the energy storage device 608 are compared. In some embodiments, this comparison may be performed by the processor 711. At decision step 2718, it is determined if the voltage of the energy storage device (VBAT) is greater than the compliance voltage and/or the adjusted compliance voltage (VCOMP). If it is determined that the compliance voltage and/or the adjusted compliance voltage is greater than the voltage of the energy storage device 608, or in other words that the battery voltage is less than the compliance voltage and/or the adjusted compliance voltage, then the process 2700 continues to block 2720 and stimulation voltage generation is continued with the voltage decreasing circuit such as, for example, with the boost converter 804.

Returning again to decision step 2718, if it is determined that the compliance voltage and/or the adjusted compliance voltage is less than the voltage of the energy storage device 608, or in other words, that the battery voltage is greater than the compliance voltage and/or the adjusted compliance voltage, then the process 2700 proceeds to block 2722 wherein the error value is compared to maximum error threshold. In some embodiments, the maximum error threshold may identify a maximum error value, which may be a percent of the set current. In some embodiments, this maximum error value may be, for example, between 5% and 40% of the set current, between 10% and 30% of the set current, approximately 20% of the set current, approximately 15% of the set current, between approximately 50 μA and 200 μA, approximately 100 μA, or any other or intermediate value or percent. This comparison may be performed by the processor 711.

At decision step 2724, it is determined if the maximum error threshold is exceeded. In other words, it is determined if the difference between the set current and the actual current measured through the current source 736 is greater than the maximum error threshold, or is less than the maximum error threshold. If it is determined that the difference between the set current and the actual current measured through the current source 736 is greater than the maximum error threshold, or in other words, that the maximum error threshold is exceeded, then the process 2700 proceeds to block 2720 and continues stimulation voltage generation with the voltage increasing circuit such as, for example, with the boost converter 804.

Alternatively, if it is determined that the difference between the set current and the actual current measured through the current source 736 is less than the maximum error threshold, or in other words, that the maximum error threshold is not exceeded, then the process 2700 proceeds to block 2708 and the voltage decreasing circuit, for example, the buck converter 800 is selected for generation of the stimulation voltage. In some embodiments, block 2708 may further include generation of the stimulation voltage.

Figure 12:
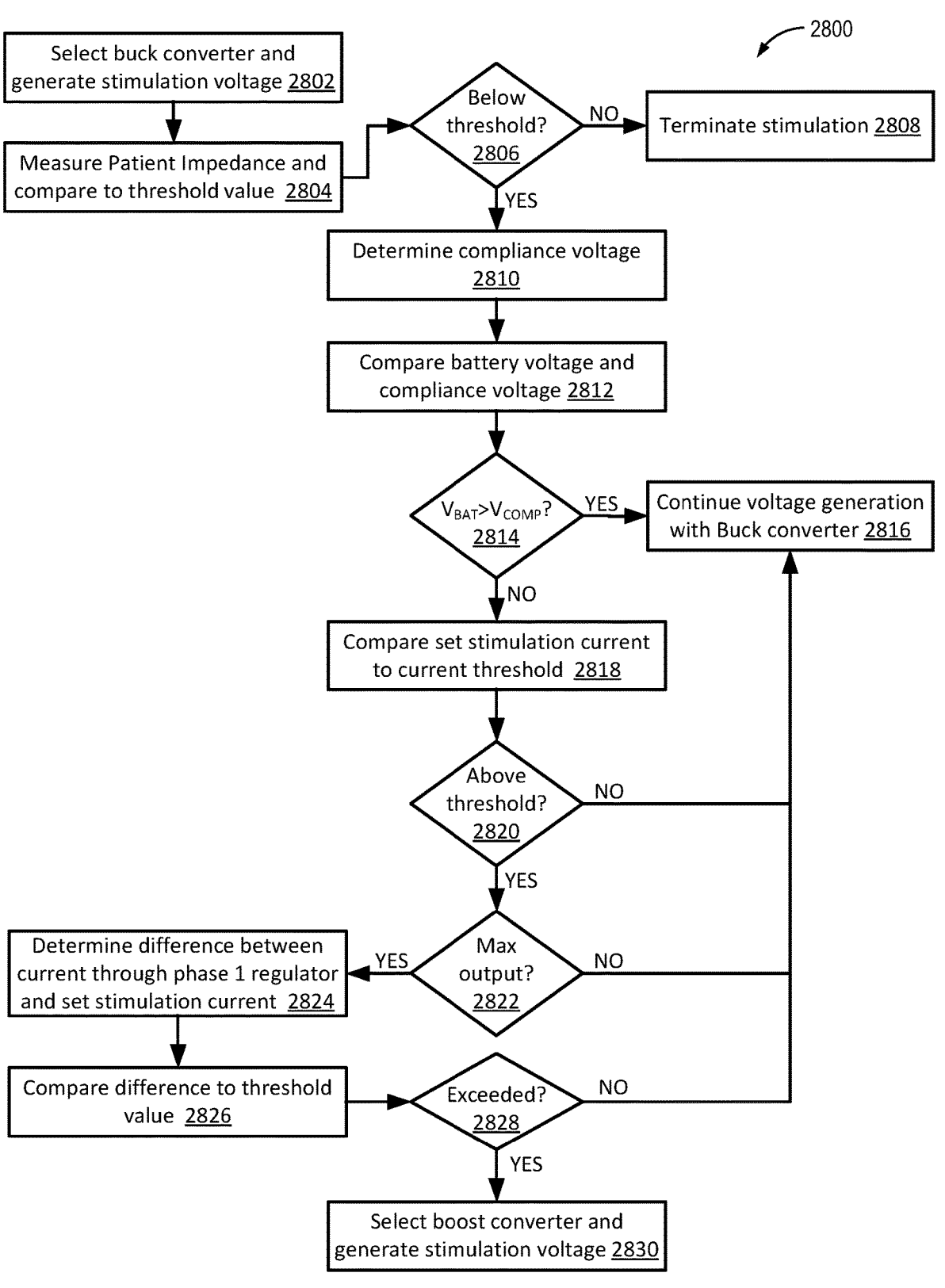
FIG. 12 shows a flowchart illustrating one embodiment of a process for determining whether to switch from stimulation voltage generation with a voltage decreasing circuit to the voltage increasing circuit.

With reference to FIG. 12, a flowchart illustrating one embodiment of a process 2800 for selecting one of voltage decreasing circuit such as, for example, the buck converter 800 and the voltage increasing circuit such as, for example, the boost converter 804 for generation of the stimulation voltage, and specifically for determining whether or not to switch from stimulation voltage generation with voltage decreasing circuit to the voltage increasing circuit is shown. In some embodiments, the process 2800 may be performed as a part of, or in the place of the step of block 2506 of process 2500. In some embodiments, the process 2800 may be performed, in addition to the process 2700, as a part of, or in the place of the step of block 2506 of process 2500. The process 2800 may be performed by all or portions of the IPG 10, including by the processor 711.

The process 2800 begins at block 2802, wherein the voltage decreasing circuit, and in some embodiments, the buck converter 800 is selected for generation of the stimulation voltage. In some embodiments, the voltage decreasing circuit may be selected as indicated by steps 2702 through 2708 of process 2700.

At block 2804, patient impedance is measured and compared to a threshold value. In some embodiments, the patient impedance may be measured and compared to a threshold value to determine if the patient impedance exceeds the threshold value. In some embodiments, the patient impedance threshold may identify an impedance level corresponding to an open circuit or to a short circuit. This threshold may be, for example, between 1,000 ohms and 10,000 ohms, between 2,000 ohms and 8,000 ohms, between 3,000 ohms and 7,000 ohms, between 4,000 ohms and 6,000 ohms, approximately 5,000 ohms or any other or intermediate value. The comparison between the measured patient impedance and the threshold value may be performed by the processor 711.

At decision state 2806, it is determined if the measured patient impedance is below the threshold value. In some embodiments, this determination may be made based on the comparison of block 2804. If it is determined that the measured patient impedance is greater than, or in some embodiments, greater than or equal to the threshold value, then the process 2800 proceeds to block 2808 and stimulation is terminated. In some embodiments, and as part of block 2808, an indicator of an error may be generated and/or an error counter may be incremented.

Returning again to decision state 2806, if it is determined that the measured patient impedance is below the threshold, then the process 2800 proceeds to block 2810, the compliance voltage and/or the adjusted compliance voltage is determined. In some embodiments, the compliance voltage may be adjusted due to the voltage drop across the current source 736, and specifically across the phase one current source 740. This may include the voltage drop across the pair of cascode arranged transistors 1400 in the phase one current source 740 and across the regulation resistor 1406 in the phase one current source 740.

At block 2812, the voltage of the energy storage device 608 and the compliance voltage and/or the adjusted compliance voltage are compared. In some embodiments, the voltage of the energy storage device 608 may be the battery voltage. The voltage of the energy storage device 608 may be compared to the compliance voltage and/or the adjusted compliance voltage by the processor 711.

At decision step 2814, it is determined if the voltage of the energy storage device 608 is greater than the compliance voltage and/or the adjusted compliance voltage. This determination may be made based on the comparison of block 2812. If it is determined that the voltage of the energy storage device 608 is greater than the compliance voltage and/or the adjusted compliance voltage, then the process 2800 proceeds to block 2816, wherein the voltage decreasing circuit, and specifically the buck converter 800 continues to generate the stimulation voltage.

Returning again to decision step 2814, if it is determined that the voltage of the energy storage device 608 is less than the compliance voltage and/or the adjusted compliance voltage, then the process 2800 proceeds to block 2818, wherein the set stimulation current is compared to a current threshold. In some embodiments, the current threshold may delineate between stimulation currents for which the voltage decreasing circuit, and specifically the buck converter 800 is used to generate the stimulation voltage and stimulation currents for which the voltage increasing circuit, and specifically boost converter 804 is used to generate the stimulation voltage. In some embodiments, the current threshold may identify a stimulation current of approximately 200 µA, approximately 300 µA, approximately 400 µA, approximately 500 µA, approximately 600 µA, approximately 700 µA, approximately 800 µA, between approximately 300 µA and 600 µA, or any other or intermediate stimulation current.

At decision step 2820, it is determined if the stimulation current is above the current threshold. In some embodiments, this determination may be based on the comparison of block 2818. If it is determined that the stimulation current is not above the current threshold, or in other words, that the stimulation current is below the current threshold, then the process 2800 proceeds to block 2816, wherein the voltage decreasing circuit, and specifically the buck converter 800 continues to be used to generate the stimulation voltage.

Returning again to decision step 2820, if it is determined that the stimulation current is above the current threshold, or in other words, is greater than the current threshold, then the process 2800 continues to decision step 2822, wherein it is determined if the voltage decreasing circuit, and specifically the buck converter 800 is already generating its maximum stimulation voltage. In some embodiments, this may include determining if the output of the voltage decreasing circuit, and specifically of the buck converter 800 may be increased, or if the headroom of the voltage decreasing circuit, and specifically of the buck converter 800 may be increased. If it is determined that the voltage decreasing circuit, and specifically the buck converter 800 is not generating its maximum stimulation voltage, then the process 2800 may proceed to block 2816, wherein the voltage decreasing circuit, and specifically the buck converter 800 continues to be used to generate the stimulation voltage.

Alternatively, if it is determined that the voltage decreasing circuit, and specifically the buck converter 800 is already generating its maximum stimulation voltage, then the process 2800 proceeds to block 2824, wherein a difference between the actual stimulation current and the set stimulation current is determined. In some embodiments, this determination may be performed in the same manner as determining the error value in block 2606 of process 2600.

At block 2826, the error value, or in other words, the difference between the actual stimulation current and the set stimulation current, which may be current through the phase one current source 740, and the set stimulation current is compared to a threshold value. In some embodiments, the threshold value may delineate between acceptable differences between the actual stimulation current and the set stimulation current, and unacceptable differences between the actual stimulation current and the set stimulation current. In some embodiments, this threshold value may be a value between 5% and 40% of the set current, between 10% and 30% of the set current, approximately 20% of the set current, approximately 15% of the set current, between approximately 50 µA and 200 µA, approximately 100 µA, or any other or intermediate value or percent.

At decision step 2828, it is determined if the threshold value of block 2826 is exceeded. In some embodiments, this determination may be made based on the comparison of block 2826. If it is determined that the difference is less than the threshold value, or in other words, that the difference between the actual stimulation current and the set stimulation current is acceptable, then the process 2800 proceeds to block 2816, wherein the voltage decreasing circuit, and specifically the buck converter 800 continues to generate the stimulation voltage.

Returning again to decision step 2828, if it is determined that the threshold value is exceeded by the difference between the actual stimulation current and the set stimulation current, or in other words, that the difference between the actual stimulation current and the set stimulation current is unacceptable, then the process 2800 proceeds to block 2830, wherein the voltage increasing circuit, and specifically the boost converter 804 is selected for generation of the stimulation voltage.

In the foregoing specification, various non limiting exemplary embodiments are disclosed. Various features and aspects of the disclosed embodiments may be used individually or jointly. Further, the various disclosed embodiments may be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of the neurostimulator as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

Various disclosed embodiments may be described as set forth below.

What is claimed is:

1. An energy efficient device for delivering one or more electrical pulses to a target region within a patient's body, the device comprising:
   a housing;
   a controller located in the housing;
   an energy source located in the housing; and
   a stimulation circuit located in the housing, wherein the stimulation circuit generates a stimulation current that provides the one or more electrical pulses, and wherein the stimulation circuit includes a current source;
   wherein the energy source provides a voltage to the stimulation circuit;
   wherein the current source includes a pair of cascode arranged transistors that are controlled to maintain an amplitude of the stimulation current substantially constant, wherein the controller is configured to control the stimulation circuit to minimize the voltage across one of the pair of cascode arranged transistors in order to reduce an amount of energy withdrawn from the energy source while the current source operates to provide the substantially constant stimulation current.

2. The energy efficient device of claim 1, wherein the stimulation current includes a set of phases including at least a first phase and a second phase and wherein the current source includes a set of current sources corresponding to each phase in the set of phases including at least a phase one current source and a phase two current source.

3. The energy efficient device of claim 2, wherein the phase one current source includes the pair of cascode arranged transistors, and the phase two current source includes an additional pair of cascode arranged transistors.

4. The energy efficient device of claim 3, wherein a transistor of the pair of cascode arranged transistors of the phase one current source includes a first control input configured to control the current allowed through the pair of cascode arranged transistors of the phase one current source.

5. The energy efficient device of claim 4, wherein the first control input is controlled via a first control voltage applied to the first control input, wherein the control voltage is maintained by a control voltage holding capacitor coupled to the first control input of the transistor of the pair of cascode arranged transistors of the phase one current source.

6. The energy efficient device of claim 5, wherein the control voltage corresponds to the amplitude of the stimulation current.

7. The energy efficient device of claim 4, wherein a transistor of the additional pair of cascode arranged transistors of the phase two current source includes a second control input configured to control the current allowed through the additional pair of cascode arranged transistors of the phase two current source.

8. The energy efficient device of claim 1, further comprising wherein a gate input of one of the pair of cascode arranged transistors receives a control voltage that directly defines the amplitude of the stimulation current, the control voltage being maintained by a capacitor coupled to the gate input so as to hold the bias voltage applied to that transistor.

9. An implantable neurostimulator for delivering an electrical pulse to a target region within a patient's body, the neurostimulator comprising:

a housing;
  a controller located in the housing;
  an energy source located in the housing;
  a stimulation circuit located in the housing, wherein the stimulation circuit generates a stimulation current that provides the electrical pulse, wherein the stimulation circuit includes:
    a converter for generating the stimulation current;
    a current source in electrical communication with the converter; and
  wherein the current source includes a pair of cascode arranged transistors that are controlled to maintain an amplitude of the stimulation current substantially constant, wherein the controller is configured to control the pair of cascode transistors to minimize a voltage across one of the pair of cascode arranged transistors in order to reduce an amount of energy withdrawn from the energy storage device while the current source operates to provide the substantially constant stimulation current.

10. The neurostimulator of claim 9, wherein the stimulation current has two phases and wherein the current source includes a phase one current source and a phase two current source.

11. The neurostimulator of claim 10, wherein the phase one current source includes the pair of cascode arranged transistors, and the phase two current source includes an additional pair of cascode arranged transistors.

12. The neurostimulator of claim 11, wherein a transistor of the pair of cascode arranged transistors of the phase one current source includes a first control input configured to control the current allowed through the pair of cascode arranged transistors of the phase one current source.

13. The neurostimulator of claim 12, wherein the first control input is controlled via a first control voltage applied to the first control input, wherein the control voltage is maintained by a control voltage holding capacitor coupled to the first control input of the transistor of the pair of cascode arranged transistors of the phase one current source.

14. The neurostimulator of claim 13, wherein the control voltage corresponds to the amplitude of the stimulation current.

15. The neurostimulator of claim 12, wherein a transistor of the additional pair of cascode arranged transistors of the phase two current source includes a second control input configured to control the current allowed through the additional pair of cascode arranged transistors of the phase two current source.

* * * * *